United States Patent [19]

Brugge et al.

[11] Patent Number: 5,342,968
[45] Date of Patent: Aug. 30, 1994

[54] PROCESS FOR PRODUCING SULFONYLBIS (PHTHALIC ANHYDRIDE)

[75] Inventors: Stephen P. Brugge; Juergen K. Holzhauer, both of Naperville; Thomas E. Wolff, Lisle, all of Ill.

[73] Assignee: Amoco Corporation, Chicago, Ill.

[21] Appl. No.: 542,742

[22] Filed: Jun. 22, 1990

[51] Int. Cl.$^5$ .......................................... C07D 307/83
[52] U.S. Cl. ...................... 549/241; 549/248; 562/412; 562/413; 562/414
[58] Field of Search ............... 549/241, 248; 562/412, 562/413, 414

[56] References Cited

U.S. PATENT DOCUMENTS 3,022,320  2/1962  Woodbury et al. ............... 549/241
3,920,735  11/1975  Wampfler et al. ............... 549/248

*Primary Examiner*—Mukund J. Shah
*Assistant Examiner*—Y. N. Gupta
*Attorney, Agent, or Firm*—Thomas E. Nemo; James R. Henes; Wallace L. Oliver

[57] ABSTRACT

A process for making relatively high purity eulfonylbis(phthalic anhydride) is provided. 3,3',4,4'-tetramethyl diphenyl sulfone is catalytically oxidized in a solvent under liquid phase elevated temperature and pressure conditions. The catalyst is constituted by cobalt, manganese, zirconium, and bromine. Sulfonylbis(phthalic) acid is recovered by crystallization and is then heated to produce the anhydride. Preferably, the acid is purified prior to dehydration.

39 Claims, 2 Drawing Sheets

PROCESS FOR PRODUCING SULFONYLBIS (PHTHALIC ANHYDRIDE)

FIELD OF THE INVENTION

This invention relates to the preparation of sulfonylbis(phthalic anhydride) from 3,3',4,4'-tetramethyl diphenyl sulfone and includes optional purification of the intermediate sulfonyl bis(phthalic acid) prior to dehydration.

BACKGROUND OF THE INVENTION

Sulfonylbis(phthalic anhydride) (SPAN), also known as 3,3',4,4'-sulfonylbis(phthalic anhydride) and as 3,3',4,4'-diphthalic anhydride sulfone, is a useful chemical intermediate that is particularly suitable for production of polymers with enhanced physical properties. For example, such dianhydride is useful for preparing polyimides. Also, polymers incorporating such dianhydride can be prepared with useful blending properties in polyether ketone formulations. If desired, such dianhydride can be converted to an ester which can then be used in the manufacture of polymers, such as polyimide resins, and the like. For such purposes, such dianhydride typically must have relatively high purity. Also, from the standpoint of commercial practically, such product must be producible in a relatively high yield from an economical process.

One possibly promising route for the preparation of SPAN could involve the oxidation of 3,3',4,4'-tetramethyl diphenyl sulfone (TMPS), also known as 3,3',4,4'-dixylyl sulfone, to the corresponding acid, sulfonyl bis(phthalic acid) (SBPA), also known as 3,3',4,4'-sulfonyl bis(phthalic acid), 3,3',4,4'-diphthalic acid sulfone, and as bis(3,4-dicarboxyphenyl) sulfone, followed by the dehydration of this acid to the desired dianhydride. Such an alkyl aromatic oxidation process is provided by the so-called "Mid-Century Oxidation Process" which is generally described by Towle et al in "Make Most Aromatic Acids Using Mid-Century Oxidation Processes," appearing in "Petrochemical Developments," 1964 Vol. 43, No. 11, pp. 149–152. See also U.S. Pat. Nos. 3,064,044 to Baldwin, 4,081,464 to Marsh et al, and 4,587,355 to Brown et al. Also, Japanese Kokai Tokyo Koho Patent Publication No. 88,185,939 of Aug. 1, 1988, based on Japanese patent application 87/14,365 filed Jan. 24, 1987 to Nakazawa et al [also in CA 110 (14):1154920], describes a process for oxidation of TMPS to SBPA in an aqueous acetic acid/solution using a heavy metal-and-bromine catalyst system, such as a cobalt/manganese/bromine catalyst.

The Nakazawa et al disclosure contains no teaching concerning the use of a zirconium-containing catalyst, the purification of SBPA, or the direct dehydration of solid SBPA to SPAN.

When a Mid-Century oxidation of TMPS to SBPA was carried out semicontinuously with a cobalt/manganese/bromine catalyst in an acetic acid/water solution, an SBPA purity of only 81.6% was achieved (see Example 6 hereinbelow), not a sufficient purity for use in making therefrom by direct solid state dehydration SPAN for polymer applications.

The prior art processes for dehydrating a polycarboxylic acid, such as SBPA, to SPAN utilize a liquid phase process. For example, dehydration of bis(3,4-dicarboxyphenoxyphenyl) sulfone to bis(3,4-dicarboxyphenoxyphenyl) sulfone dianhydride in acetic anhydride solution is described in U.S. Pat. No. 3,812,159 to Lubowitz. Purification and/or dehydration of an aromatic polycarboxylic acid, such as SBPA, in an organic solvent in the presence of activated carbon is taught in U.S. Pat. No. 4,370,487 to Meyer et al. A thermal dehydration of impure diphenyl sulfone carboxylic acids, such as crude SBPA, is taught in "Synthesis of Diaryl Sulfones and polycarboxylic acids Based on Them" by Mironow et al in Izv. Yyosh. Ucheb. Zaved., Khim. Khim. Tekhnol., 12 (11), 1588–93 (1969), CA72 (17): 89981c. While a solid phase dehydration to a relatively high purity product would be more desirable, so far as now known, the direct solid state dehydration of already highly purified SBPA to SPAN is not taught or accomplished in the prior art.

A new and improved process for converting TMPS to SPAN in high yield and in a purity sufficient for most known polymer applications would be economically advantageous. The present invention provides such a process.

SUMMARY OF THE INVENTION

The present invention provides an economical method for producing relatively high purity sulfonyl bis(phthalic anhydride) (SPAN) in commercially desirable yields from 3,3',4,4'-tetramethyl diphenyl sulfone (TMPS). The method utilizes the steps of:
(a) catalytic oxidation of TMPS to sulfonyl bis(phthalic acid) (SBPA);
(b) recovery of SBPA; and
(c) dehydration of solid SBPA to SPAN.

The catalytic oxidation is carried out under liquid phase conditions in an oxidation solvent at a temperature in the range of about 275° F. to about 440° F. (about 135° C. to about 227° C.) and at a pressure in the range of about 100 psig to about 400 psig (about 690 kPa to about 2760 kPa), preferably at about autogenous pressure, in the presence of an oxygen-containing gas.

The oxidation catalyst system employed in the oxidation step includes a catalytically effective amount of zirconium together with conventional catalysts for the liquid phase oxidation of alkyl aromatics. A preferred catalyst system includes forms of zirconium, cobalt, manganese and bromine that are soluble in the oxidation solvent employed.

A surprising and unexpected feature of the present oxidation process is the discovery that the presence of a relatively small amount of zirconium drives the oxidation reaction towards completion and towards relatively high yields of SBPA with minimal undesirable by product production.

The oxidation solvent can be a $C_2$ to $C_6$ aliphatic acid which additionally may contain not more than about 15 weight percent water on a total solvent basis, preferably about 2 to about 10 weight percent water. The present, particularly preferred oxidation solvent is a mixture comprised, on a total solvent basis, of about 95 weight percent acetic acid and about 5 weight percent water.

As oxidation product, an effluent stream having a reduced TMPS content, but containing SBPA, is withdrawn from the oxidation zone of a reactor.

SBPA is recovered from such effluent stream by cooling such stream to a crystallization temperature for SBPA, usually below about 200° F. (about 93° C.), and preferably in the range of about 50° F. to about 125° F. (about 10° C. to about 51° C.) to crystallize the SBPA present, which is then separated therefrom.

Recovered solid SBPA is dehydrated directly from its solid state by heating to a temperature in the range of about 370° F. to about 450° F. (about 188° C. to about 232° C.), preferably about 375° F. (about 190° C.).

The production method is relatively simple, efficient, and economical. The SPAN thus produced is obtained in relatively high yield and relatively high purity.

Advantageously, the oxidation can be practiced with existing equipment usable for carrying out the well-known Mid-Century alkyl aromatic oxidation process so that capital costs for producing SBPA from TMPS can be minimized for existing installations.

Although a relatively high purity SPAN is readily producible by the practice of the present invention, for certain polymer applications an even higher purity SPAN is needed. For such purposes, the present invention provides an operational mode wherein the produced SBPA, after its recovery but before its dehydration, is purified further.

This further purification is carried out by dispersing the SBPA in a purification solvent followed by separation of the SBPA therefrom. The SBPA can be either slurried in the purification solvent followed by physical separation, or preferably dissolved in the purification solvent followed by SBPA recrystallization, and then physical separation. A combination of such procedures can be used as well. A sequence of such dispersing and separating preferably is repeated more than once. A present preference is to recrystallize SBPA from such a solution in the presence of activated carbon or similar inert absorbent material.

The resulting highly purified solid SBPA preferably is first dried and then dehydrated to SPAN. The SPAN so produced characteristically has a much higher purity than a SPAN produced from a non-purified SBPA; however, a relatively lower purity SBPA has been found to dehydrate at a faster rate.

In a presently preferred purification process, two successive purification stages are employed, each stage comprising SBPA dissolution in water followed by recrystallization and separation. An activated carbon treatment is included in the first such stage.

The process can be practiced batchwise, continuously, or semicontinuously, as desired.

Various other and further features, embodiments, and the like which are associated with the present invention will become apparent to those skilled in the art from the present description considered in conjunction with the accompanying drawings wherein presently preferred embodiments of the invention are illustrated by way of example. It is to be expressly understood, however, that the associated accompanying portions of this specification are provided for purposes of illustration and description only, and are not intended as limitations on the invention.

Figure 1:
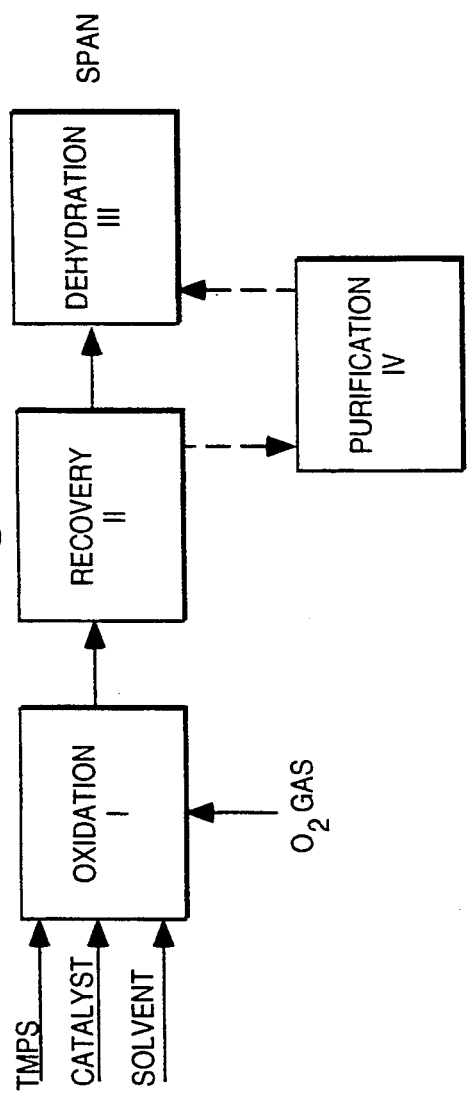
FIG. 1 is a block diagram showing the method of this invention for producing SPAN from TMPS.

DETAILED DESCRIPTION OF THE PREFERRED EMBODIMENTS (a) Overall Process Description Referring to FIG. 1, oxidation of TMPS occurs in Process Zone I in a solvent maintained in a liquid phase under elevated temperature and pressure in the presence of a dissolved, zirconium-containing catalyst and an oxygen-containing gas. A liquid phase effluent is withdrawn from Process Zone I and passes into Process Zone II wherein such effluent is cooled to crystallize and recover SBPA. Crystallized SBPA is separated from residual portions of the effluent liquid phase. Recovered SBPA then passes into Process Zone III wherein solid, crystalline SBPA is thermally dehydrated to SPAN. Optionally, but preferably, recovered crystallized SBPA from Process Zone II passes through Process Zone IV for purification before entering Process Zone III for dehydration. The respective operational conditions employed in each of Process Zones I, II, III and IV are described and illustrated hereinbelow.

Figure 2:
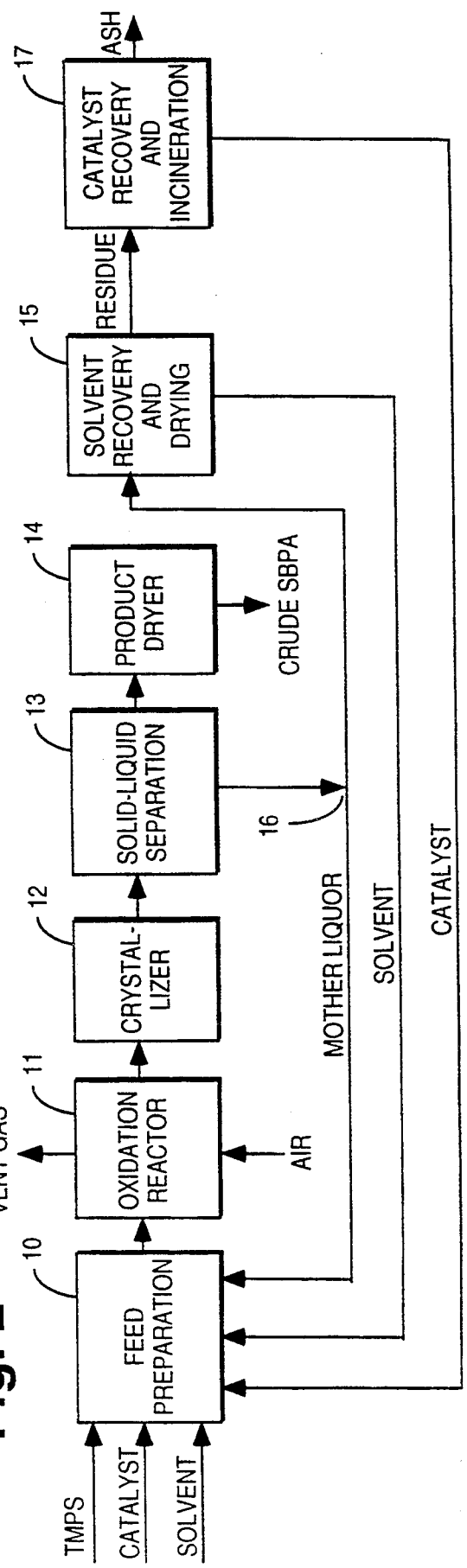
FIG. 2 is a block diagram showing a preferred process embodiment of this invention for TMPS oxidation to SBPA followed by SBPA recovery from the reaction mixture produced in such oxidation.

FIG. 2, illustrates a presently preferred embodiment of the process in Zones I and II shown in FIG. 1. Thus, at a reactor feed preparation station 10, a partial reactant mixture in liquid form is prepared. For example, station 10 can comprise an agitator equipped mixing vessel into which are charged predetermined respective quantities of TMPS, oxidation solvent, and catalyst. The catalyst is conveniently dissolved in a portion of the oxidation solvent to provide a concentrate for ease in handling including addition and mixing in station 10. If desired, such a mixing vessel can be jacketed and heated to aid mixing of the charged materials, and thereby achieve a desired uniform solution of the admixed reactants. Suitable a heating temperatures are in the range of about 100° F. to about 300° F. (about 38° C. to about 150° C). For semicontinuous oxidation the feed preparation station may be in two parts.

From feed station 10, the obtained solution is transferred to reactor station 11 which is characteristically an agitated oxidation reactor maintained at a desired elevated temperature and pressure. The reactant mixture in the oxidation reactor is maintained in a liquid phase. An oxygen containing gas, preferably air, is charged into the oxidation reactor, and admixed with the liquid phase. Residual gaseous components are vented from the oxidation reactor. Operating conditions for station 11 are elsewhere described herein.

From station 11, a reactor effluent stream is transferred to crystallizer station 12 wherein such effluent stream is cooled to a desired temperature below about 200° F. (about 93° C.), thereby causing the dissolved SBPA in the effluent stream to crystallize. The resulting slurry is then transferred to solid-liquid separator station 13 wherein the crystallized SBPA is separated from the residual effluent centrifugally. More than one centrifuge stage can be employed, if desired, at station 13.

From station 13, the separated crude SPBA is transferred to dryer station 14 wherein the SBPA is dried to remove therefrom the residual portion of the oxidation solvent.

Depending particularly upon the water content of the residual effluent, or mother liquor, recovered at station 13 after SBPA is separated, the mother liquor can either be recycled directly back to feed preparation station 10, or be cycled to an oxidation solvent recovery and drying station 15. Alternatively, the mother liquor can be split at a location 16, or the like, so that a portion thereof is passed on to station 10 while the remainder is cycled to station 15.

At station 15, solvent recovery procedures can be undertaken. For example, the mother liquor can be separated into an aqueous acetic acid solution and residue, and the solution subjected to distillation to reduce the water content thereof down to some desired level such as about 5 weight percent. The recovered solvent, containing dissolved catalyst, is then recycled back to station 10. Recovered solid residues can be transferred to a catalyst recovery and incineration station 17 where catalyst metals are recovered from ash in a known manner.

Carbon-containing contaminants in the solid residue are combusted by heating the residue in station 17 to an elevated temperature, such as one in the range of about 1200° F. to about 2200° F. (about 650° C. to about 1200° C.) for a time period in the range of about 1 second to about 1 hour, for example. Depending upon such variables as the chemical purity of the starting feedstocks, the solid particulate residue from such a heating step can comprise oxidation solvent soluble catalyst particulates which are sufficiently pure to be directly recycled to feed station 10 as oxidation catalyst components. Alternatively, such residue may be sufficiently impure to be treated as ash that is ready for disposal. Depending upon the quantity and composition of the recycled mother liquor, the recycled solvent, and the recycled catalyst, the respective quantities of fresh starting oxidation solvent and fresh catalyst components input into station 10 are adjusted accordingly so that the reactor contents in station 10 and the effluent passing from station 10 to station 11 have a defined, desired composition.

Figure 3:
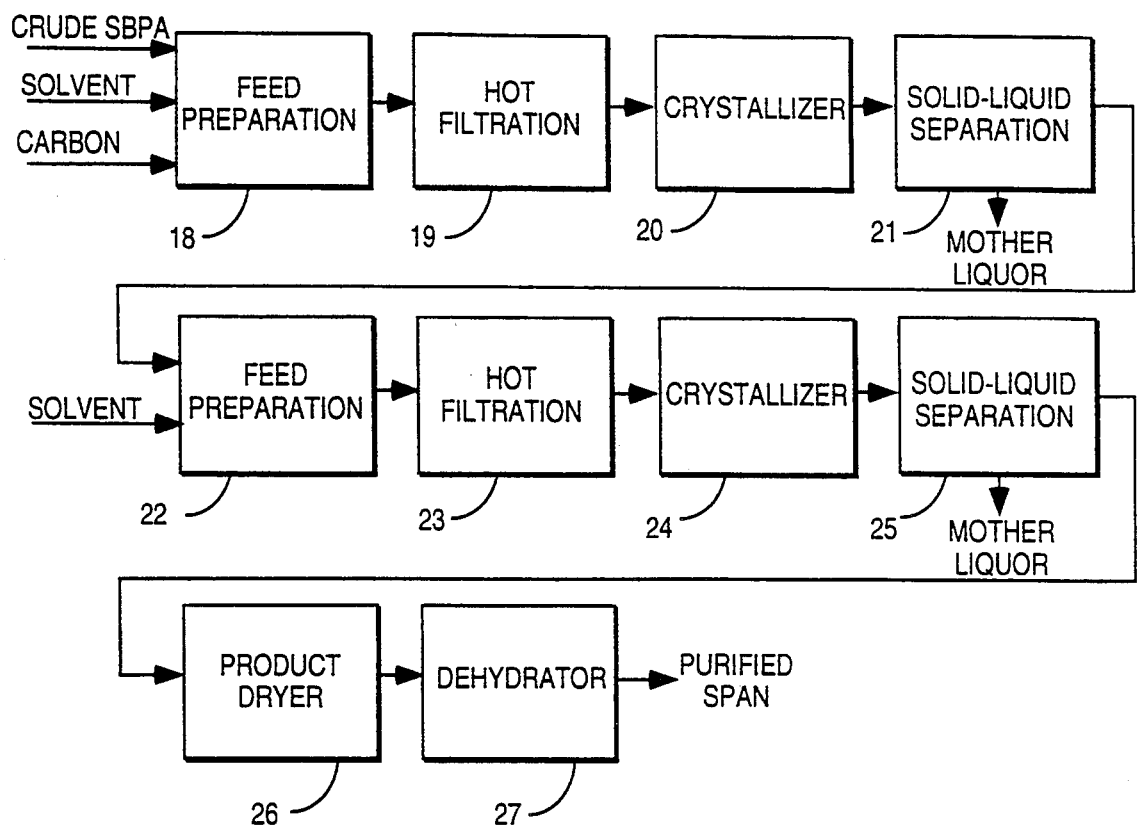
FIG. 3 is a block diagram showing a preferred process embodiment of this invention for a purified, dried, and dehydrated SPAN from a recovered SBPA produced by the process embodiment of FIG. 2.

FIG. 3 presents a flow diagram of a presently preferred purification process sequence in Zone IV followed by dehydration in Zone III as shown in FIG. 1. The solid crude SBPA from dryer station 14 (FIG. 2) is fed to a feed preparation station 18 (FIG. 3) along with selected amounts of purification solvent and activated carbon. Mother liquor from Process Zone II, fresh solvent, or mixtures thereof can be utilized for this purpose. Station 18 can be an agitator-equipped, pressurizable mixing vessel. Such a vessel is heated to a temperature in the range of about 176° F. to about 302° F. (about 80° C. to about 150° C.) under autogenous pressures sufficient to maintain a liquid phase therein. For convenience, the activated carbon can be preliminarily dispersed in the purification solvent to provide a suspension concentrate that is then added to the mixing vessel. Preferably, a filter aid such as diatomaceous earth is also added to facilitate subsequent removal of the activated carbon.

The resulting solution of the SBPA in the purification solvent with suspended activated carbon, and optional filter aid, therein is transferred from station 18 to hot filtration station 19 wherein the solution is passed through a filter bed to separate insoluble particles including the activated carbon therefrom. Station 19 is pressurized comparably to station 18.

From station 19, the filtered SBPA solution is transferred to crystallization station 20. The effluent stream from station 19 is cooled to a desired temperature below about 200° F. (about 93° C.), thereby causing the dissolved SBPA in such effluent stream to crystallize. The resulting slurry is then transferred to solid-liquid separation station 21 wherein the recrystallized SBPA is separated from the residual mother liquor effluent by filtration, centrifugation, or like expedient. Preferably, the obtained filter cake is washed with fresh solvent to displace residual mother liquor therefrom.

From station 21, the separated SBPA is transferred to another feed preparation station 22. Fresh purification solvent is also charged to station 22 in a selected amount. Station 22, for example, can, like station 18, comprise an agitator equipped, pressurizable mixing vessel. Such a vessel is heated to a temperature in the range of about 176° F. to about 266° F. (about 80° C. to about 130° C.) under autogenous pressures sufficient to maintain a liquid phase therein. No activated carbon is present at this station.

The resulting solution of the SBPA in the purification solvent is transferred from station 22 to hot filtration station 23 to separate insoluble particulates therefrom. Station 23 is pressurized comparably to station 18.

From station 23, the filtered SBPA solution is transferred to crystallizer station 24. The effluent stream from station 23 is depressurized and cooled to a desired temperature below about 200° F. (about 93° C.), thereby causing the dissolved SBPA in such effluent to recrystallize again. The resulting slurry is then transferred to solid-liquid separator station 25 wherein the recrystallized SBPA is separated from the residual mother liquor effluent by filtration, centrifugation, or like manner.

From station 25, the separated and purified SBPA is transferred to dryer station 26 wherein the SBPA is dried to remove therefrom residual portions of the purification solvent.

From station 26, the dried and purified, solid SBPA is transferred to dehydration station 27 wherein the SBPA is heated, while maintaining solid state conditions for SBPA, at an elevated temperature for a time sufficient to dehydrate the SBPA and convert same to SPAN of high purity.

(b) Catalytic Oxidation of TMPS

To oxidize TMPS to SBPA in accord with the present invention, TMPS is heated in a reaction zone under liquid phase conditions and in the presence of a zirconium-containing oxidation catalyst. The following materials are charged to the reaction zone:
3,3',4,4'1 -tetramethyl phenyl sulfone (TMPS),
oxidation solvent containing at least one aliphatic carboxylic acid having from 2 to 6 carbon atoms per molecule,
oxidizing gas, such as oxygen, air, or the like oxygen-containing gas,
zirconium containing oxidation catalyst.

The TMPS employed as a starting material in the practice of the process of this invention may be prepared by any desired procedure known in the art. For example, TMPS can be prepared from o-xylene and sulfuric acid, chlorosulfonic acid, or thionyl chloride under reflux conditions at atmospheric pressure. Metal catalysts promote this particular reaction.

Preferably, the starting TMPS has a purity of at least about 96 weight percent, and more preferably has a purity of at least about 99 weight percent.

The oxidation solvent can optionally contain up to about 15 weight percent water on a total solvent weight basis. A present preference is to employ an oxidation solvent composition initially comprised of a mixture of such an aliphatic carboxylic acid and water wherein, on a 100 weight percent total initial oxidation solvent composition basis, the quantity of such aliphatic acid is in the range of about 98 to about 90 weight percent, and, correspondingly, the quantity of water is in the range of about 2 to about 10 weight percent. Examples of suitable aliphatic acids which may be employed as solvents or as cosolvents in the practice of the process of this invention include acetic acid (presently preferred), propionic acid, n-butyric acid, isobutyric acid, n-valeric acid, trimethylacetic acid, caproic acid, and the like. Although water can be present, it is preferably present in the oxidation solvent only to a minimum extent that is within the range above indicated. A presently most preferred starting oxidation solvent comprises about 95 weight percent acetic acid and about 5 weight percent water on a total solvent weight basis.

The final weight ratio of the oxidation solvent to the TMPS in the reaction zone is in the range of about 2:1 to about 10:1, and more preferably is in the range of about 3:1 to about 8:1. In the case of aqueous acetic acid as the oxidation solvent, the weight ratio of oxidation solvent to TMPS is preferably about 5.

The amount of oxygen-containing gas charged to the reaction zone is at least sufficient to achieve and maintain during the oxidation a molar excess of oxygen relative to the TMPS present; i.e., the mole ratio of oxygen to TMPS preferably is about 6:1 and greater.

Any convenient source of molecular oxygen may be employed for the oxidation process of this invention. Air is presently preferred as such source. The oxygen content of the molecular oxygen source can vary, for example, from that of the oxygen content of atmospheric air up to that of industrial grade oxygen and above. Oxygen-enriched air can be utilized as well.

The oxidation catalyst is constituted by cobalt, manganese, zirconium, and bromine components, all of which are soluble in the oxidation solvent. Preferably, these catalyst components are preliminarily dissolved in the oxidation solvent (or a portion of the solvent) before being charged to the reaction zone. The respective amounts of each of the components is chosen so that there are present in the reaction zone about a 4 to about 300 milligram atoms of cobalt calculated as elemental cobalt per gram mole of TMPS, or about 0.02 to about 1 weight percent of cobalt in the catalyst composition dissolved in the oxidation solvent, on a 100 weight percent total weight basis. In addition, in such solution composition, the mole ratio of manganese to cobalt, calculated as elemental manganese and as elemental cobalt, is in the range of about 0.5 to about 5, the mole ratio of zirconium to cobalt, calculated as elemental zirconium and elemental cobalt, is in the range of about 0.01 to about 0.1, and the mole ratio of bromine, calculated as elemental bromine, to the sum of all metals (that is, cobalt, manganese, and zirconium) is in the range of about 0.5 to about 2.

The use of zirconium in combination with the other catalyst components is believed to drive the oxidation of TMPS towards completion, and thus to provide relatively high yields of SBPA with a minimum of undesirable by-product production. TMPS oxidation using a catalyst system as provided herein, but at a zirconium level that is less than that above indicated, can result in relatively high levels of partial oxidation products, undesirably high optical densities, and relatively low yields of SBPA. When zirconium is absent from the catalyst system, carbon oxide formation is reduced, but SBPA yields fall and a corresponding decrease in triacid by-product impurities is not observed. Zirconium levels to values above those above indicated for TMPS oxidation do not further improve oxidation efficacy.

An exemplary, and presently most preferred, catalyst system for use with an oxidation solvent comprised of about 95 weight percent acetic acid and about 5 weight percent water comprises, on a total solution basis in such solvent, about 0.2 weight percent dissolved cobalt, an amount of dissolved manganese sufficient to produce a manganese to cobalt molar ratio of about 2, an amount of dissolved zirconium sufficient to produce a zirconium to cobalt molar ratio of about 0.03, and an amount of dissolved bromine sufficient to produce a bromine to total metals (that is, cobalt, manganese and zirconium) molar ratio of about 1.

In general, a catalyst system used in the practice of the process of the present invention is provided by a combination of solvent soluble catalyst components of the type heretofore conventionally used for liquid phase oxidation of alkyl aromatics, such as those comprised of a mixture of solvent soluble compounds of cobalt, manganese and bromine, plus at least one solvent soluble zirconium compound.

In a preferred embodiment of the method of this invention, the oxidation solvent is a mixture of acetic acid with water, such as above described, in which bromine and each of the metals cobalt, manganese, and zirconium are dissolved, such solutes being provided in any of their known acetic acid-soluble ionic or combined forms. For example, the cobalt and the manganese can each be introduced as the carbonate, the acetate tetrahydrate, and/or the bromide. Zirconium can be added in any form that is soluble in the oxidation solvent. For example, $ZrO_2$ is commercially available from the Sheppard Chemical Company, Cincinnati, Ohio, as a solution in acetic acid, and such composition is very well suited for use in the practice of this invention. The zirconium can likewise be introduced, if desired, as the carbonate, the acetate tetrahydrate, and/or the bromide.

Because of (1) the aforesaid requirements regarding the mole ratio of bromine to cobalt and manganese (each calculated as the elemental metal), and (2) the fact that the bromides of zirconium, cobalt and manganese inherently have a bromide to metal gram atom ratio of about 2:1, an embodiment of a catalyst system used in this invention cannot be provided by the use of only bromides of zirconium, cobalt, and manganese. Rather, a desired catalyst system is provided by selecting appropriate ratios of such bromide salts and other aliphatic carboxylic acid soluble salt forms (preferably acetate salt forms). For example, the appropriate mole ratio (above indicated) of zirconium to cobalt is conveniently providable by the use of a combination of such carboxylic acid salts (acetates preferred) and bromide salts.

Suitable bromine sources include, for example, elemental bromine ($Br_2$), ionic bromide (for example, HBr, NaBr, KBr, and the like), or organic bromides, such as those which are known to provide bromide ions at the operating temperatures employed in the present liquid phase oxidation. Examples of such organic bromides include bromobenzenes, benzylbromide, mono-and dibromo acetic acid, bromoacetyl bromide, tetrabromoethane, ethylene-di-bromide, and the like. The total bromine content (consisting of the total molecular bromine and ionic bromide) in the solvent medium is used to provide the desired ratio of elemental bromine to total cobalt and manganese in the mole ratio indicated above. The quantity of bromide ion released from the organic bromides at the oxidation operating conditions can be readily determined by known analytical means. For example, tetrabromoethane, at temperatures in the range from about 172° C. to about 225° C. (about 339° F. to about 437° F.), yields in a reaction mixture such as above described about 3 gram atoms of bromine per gram mole of tetrabromoethane.

The foregoing preferred and most preferred oxidation feed conditions (including catalyst system) are summarized in Table I, below.

TABLE I

OXIDATION FEED CONDITIONS

| Variable | Preferred Range | Most Preferred Range |
|---|---|---|
| Catalyst | | |
| Co (wt. %)[1] | 0.02–1.0 | 0.2 |
| Mn/Co (molar ratio)[2] | 0.5–5 | 2.0 |
| Zr/Co (molar ratio)[3] | 0.01–0.1 | 0.03 |
| Br/metals (molar ratio)[4] | 0.5–2 | 1 |
| Initial Solvent | | |
| H$_2$O (wt. %)[5] | 2–10 | 5 |
| solvent/TMPS (wt. ratio)[6] | 3–8 | 5 |

Table I Footnotes
[1]Weight percent of cobalt calculated as elemental cobalt in 100 weight percent of a starting solution comprised of oxidation solvent containing dissolved ionic forms of cobalt, manganese, zirconium and bromium.
[2]Molar ratio of dissolved manganese to dissolved cobalt calculated as elemental manganese and elemental cobalt.
[3]Molar ratio of dissolved zirconium to dissolved cobalt calculated as elemental manganese and elemental cobalt.
[4]Molar ratio of dissolved bromine to dissolved (cobalt plus manganese plus zirconium) calculated as elemental bromine, cobalt, manganese, and zirconium.
[5]Weight percent of water in an oxidation solvent comprised of water and acetic acid on a 100 weight percent basis.
[6]Weight ratio of oxidation solvent as defined above in Footnote (5) to TMPS in reaction zone.

During the oxidation of TMPS, the above indicated combination of materials is maintained in the reaction zone at a temperature in the range of about 275° F. to about 440° F. (about 135° C. to about 227° C.), and preferably about 350° F. to about 425° F. (about 177° C. to about 218° C.), and at a pressure in the range of about 100 psig to about 400 psig (about 690 kPa to about 2760 kPa), preferably about 150 psig to about 350 psig (about 1034 kPa to about 2413 kPa). The pressures maintained in the reaction zone at a given temperature are at least sufficient to maintain liquid phase conditions. These pressures are typically and conveniently autogenous pressures for the reaction zone composition. During the oxidation, the components in the reaction zone are stirred using an agitator means, such as a conventional impeller, or the like. A temperature and a pressure such as above indicated are preferably maintained for a time sufficient to oxidize at least about 75 mole percent of the charged TMPS, although higher and lower conversions can be achieved, if desired. For startup, the reactor can be pressurized to the desired pressure with an inert gas such as nitrogen.

The oxidation process of the present invention can be practiced batchwise, continuously, or semicontinuously, as desired.

The oxidizing gas, preferably air, is charged to the reactor to effect oxidation. For example, an initial feed rate for air is conveniently in the range of about 5 to about 10 SCFH per pound of TMPS per hour. As reactor temperature increases to a value in the range above indicated, an air feed rate is preferably increased to a substantially higher value, conveniently in the range of about 40 to about 100 SCFH per pound of TMPS per hour.

Even under batch operating conditions, it is preferred to introduce oxygen-containing gas continuously into, and to withdraw gaseous effluent continuously from an agitated reaction zone. This procedure is desirable so as to maintain relatively high oxygen partial pressures in the reaction zone. Such excesses have the beneficial effects of reducing undesirable side reactions and also of favoring formation of the desired SBPA. It is presently more preferred that the oxygen-containing gas be fed to the reaction zone at a rate which results in an exhaust (i.e. vent) gas-vapor mixture containing about 2 to about 6 volume percent oxygen.

The preferred and the presently most preferred oxidation process conditions are summarized in Table II, below.

TABLE II

OXIDATION PROCESS CONDITIONS

| Variable | Preferred Range | Most Preferred |
|---|---|---|
| Steady-state temp., °F. | 340–440 | 375 |
| Pressure, psig | 100–400 | 205 |
| Hydrocarbon add'n time, hrs | 0.5–3.0 | 1.25 |
| Vent oxygen, vol. percent | 6+ | 9 |

More preferably, the residence time of the components in the reaction zone at the particular preferred elevated temperatures and pressures employed in oxidation is sufficient to accomplish a conversion of at least about 85 weight percent of the TMPS (based on charged weight of such starting compound).

In general, the amount of by-product produced is preferably less than about 4 mole percent, and, more preferably, is kept at less than about 2 mole percent, based on starting TMPS. As the Examples set forth hereinbelow indicate, semicontinuous oxidations with reactor yields greater than about 85 mole percent can be readily obtained.

The oxidation reaction of TMPS to SBPA that is accomplished in the reaction zone proceeds relatively quickly. A substantial portion of the heat generated by the exothermic oxidation reaction is removed from the reaction mixture by vaporization of the solvent, and, to a smaller extent, of the TMPS. The vaporized material and any unreacted oxygen and other gaseous components of, for example, an air feed to the reaction zone, pass preferably upwardly through the reaction zone and are withdrawn from the reaction zone above the level of the liquid reaction mixture in the reaction zone. The gaseous effluent from the reaction zone is passed through a reflux condenser, or the like, wherein the vaporized solvent and TMPS are condensed for recycle or reuse. The non-condensable gases are conveniently vented.

When, for example, a continuous oxidation process is contemplated, the feed stream(s) introduced into the reaction zone preferably contain(s) each of the TMPS and the catalyst system already dissolved in solvent. The weight ratio of the solvent-containing dissolved catalyst and dissolved TMPS fed into the reaction zone to the total amount of solvent introduced into the reaction zone is adjustable, but a present preference is to employ a ratio of solvent to TMPS in the range of about 3:1 to about 8:1 in the reaction zone. If desired, the TMPS and the catalyst can be introduced into the reaction zone separately from the solvent rather than being preliminarily dissolved in the solvent charged in a feed stream. A molar excess of oxygen relative to TMPS is maintained.

An illustrative and presently preferred resulting liquid effluent from the oxidation reaction zone comprises, on a 100 weight percent total basis, about 15 to about 35 weight percent SBPA, about 65 to about 85 weight percent total solvent comprised of water and aliphatic carboxylic acid (preferably acetic acid), less than about 1 weight percent of unreacted TMPS, about 5 to about 10 weight percent of oxidation catalyst components, and up to about 5 weight percent of other reaction by-products. Other effluent compositions however, can be achieved without departing from the spirit and scope of the process of this invention.

As regards TMPS oxidation, the effects of changes in such variables as temperature, concentration of individual catalyst components, certain impurity concentrations, feed rates, operational mode (batch or semicontinuous), catalyst staging, and the like, upon SBPA-containing oxidation reactor effluent were investigated. Examples presented below illustrate such investigation and the present invention.

In particular, Table IVA presents illustrative data obtained in Examples 1-3 and indicates how temperature in the reaction zone affects the oxidation results. Partial oxidation products were highest in the 350° F. (177° C.) run, and essentially the same for the 375° F. (190° C.) and 400° F. (204° C.) runs. Carbon oxide production and decarboxylation product levels were highest at 400° F. (204° C.). The 350° F. (177° C.) and 375° F. (190° C.) runs had equivalent yields. A 375° F. (190° C.) oxidation temperature is most preferred because of the relatively lower levels of partial oxidation products.

Table IVB presents data obtained in Examples 4 and 5 and shows the results obtained using lower and higher catalyst levels relative to the base level of Example 1. At half the base level catalyst concentration, the carbon oxides decreased slightly, but the partial oxidation products increased by an order of magnitude. Doubling of the catalyst concentration did not have a significant effect.

Table IVC presents data obtained in Examples 6, 7, and 8, and shows the effect of zirconium on the oxidation of TMPS. Oxidations with zirconium levels a less than the levels in the base case (Example 1) result in relatively high levels of partial oxidation products, relatively high optical densities, and relatively low yields. Carbon oxide formation was reduced when zirconium was eliminated, but a corresponding decrease in the triacid impurities was not noted. SBPA yield was a only 68.1% (Example 6) when zirconium was eliminated. Increasing zirconium levels above the recommended base case levels did not further improve the oxidation process.

Table IVD presents data obtained in Examples 9 and 10 and shows the effect of bromine levels on TMPS oxidation. Reduction of bromine levels reduced carbon oxide production, but increased partial oxidation products with attendant decrease in yield. Other factors remained relatively unchanged when bromine levels were changed.

Table IVE presents data obtained in Examples 11, 12, 13, and 14. This data show the results of changing the hydrocarbon feed rate and the oxidation mode. Levels of impurities apparently resulting from decarboxylation and breakage at the sulfone group were theorized to be dependent on product residence time in the reactor. To evaluate this theory, an oxidation was made with a faster hydrocarbon feed rate, but same final solvent ratio (Example 11). No improvements were seen.

In the oxidation of Example 13, the catalyst addition was staged. In such procedure, initially only one-half of the catalyst was added. The other half of the catalyst was added continuously over the second half of the oxidation. The product of this oxidation exhibited relatively high levels of partial oxidation and decarboxylation products. Hence, staged catalyst addition appears to be undesirable in the practice of this invention.

The oxidation of Example 13 was run in a manner similar to the oxidation of Example 1 except that the oxidation temperature was allowed to increase to 380° F. (193° C.) during the last 10 minutes of hydrocarbon addition. Raising the temperature at the end decreased the partial oxidation products and maintained low carbon oxide production levels. The overall yield was not improved over the base case run of Example 1, however.

The oxidation of Example 14 was run in the batch mode. The temperature was slowly increased from about 280° F. to about 380° F. (about 138° C. to about 193° C.) during the run. The yield and quality of the cake of crude crystallized SBPA obtained was good, but not significantly better than the cake obtained using the base case (Example 1) conditions.

(c) SBPA Recovery

At the above indicated oxidation temperatures, the SBPA is completely in solution in the liquid phase reactor effluent. The SBPA begins to crystallize in such effluent when the temperature of such effluent is below about 200° F. (about 93° C.).

The quantity of SBPA so crystallized increases as the temperature decreases. At about 100° F. (about 38° C.), for example, SBPA yields averaged 3% lower than at 75° F. (about 20° C.).

However, below about 50° F. (about 10° C.), the SBPA appears to become increasingly contaminated with impurities. The crystallization temperature is preferably in the range of about 50°0 F. to about 125° F. (about 10° C. to about 51° C.), more preferably in the range of about 75° F. to about 80° F. (about 24 ° C. to about 27° C.), and most preferably is about 75° F. (about 24° C.

The SBPA is separated from the cooled effluent by any convenient procedure, including settling, filtration, centrifugation, and the like. Centrifugation is presently preferred. Typical yields of separated SBPA are in the range of about 95 percent by weight to about 110 percent by weight, based on starting TMPS.

The exemplary SBPA crude cake yields shown in the Tables IVA–IVE are based on separation at 75° F. (24° C.) using a centrifuge.

A mixture of reactor effluent containing crude SBPA crystals is preferably maintained even at a temperature that is within the above indicated cooling temperature range.

The SBPA particle size in a crude cake of SBPA so recovered is somewhat variable, but typically the mean particle size is about 16 μm.

(d) SBPA Purification

Purification of SPAN using a solvent such as water is impractical because of the inherent stability and reactivity characteristics thereof. If, for instance, an effort is made to recrystallize SPAN from water, the SPAN is hydrolyzed to SBPA. Also, purification of SPAN by dissolution and recrystallization unnecessarily raises manufacturing costs. Thus, to produce SPAN having a higher purity than that of the crude SBPA, the crude SBPA preferably is first purified to the needed extent and then dehydrated.

Crude SBPA as produced by the method of this invention can be readily purified by dispersion in a purification solvent followed by recovery therefrom. Suitable and presently preferred purification solvents include water, aliphatic carboxylic acids having from 2 to 6 carbon atoms per molecule, and mixtures thereof. Presently preferred such purification solvents are water, acetic acid, and aqueous acetic acid solutions containing about 75 to about 98 weight percent acetic acid.

Such a dispersion can be accomplished by slurrying or dissolving the SBPA crystals to be purified in the purification solvent. Recovery can be by physical separation from the slurry, or by recrystallization followed by physical separation from the mother liquor. Mixtures of such procedures, or stages, can be used, such as an sequential combination of a slurrying procedure and a recrystallization procedure, or the like. Likewise, a single stage of slurrying, or recrystallization, can be repeated more than once as part of an SBPA purification process. The temperature maintained during a slurrying procedure is preferably in the range of about 32° F. to about 167° F. (about 0° C. to about 75° C.). The temperature maintained during a dissolution procedure is in the range of about 176° F. to about 302° F. (about 80° C. to about 150° C.).

Recrystallization is presently the preferred purification procedure. Water is presently the most preferred purification solvent. When, for example, crude SBPA was slurried in water and then recrystallized from, respectively, water, 75% acetic acid with 25% water on a 100 weight percent solvent basis, and acetic acid, it was found that water removed the most 4-bromophthalic acid and residual catalyst. Also, the appearance of the cake is whiter when water is used. Other organic impurities appeared to be removed equally well by acetic acid and mixtures of 75% acetic acid with water. Purification by water recrystallization can be carried out with as well as without concurrent activated carbon treatments.

Activated carbon treatment during purification improve the optical density while not having a significant effect on other impurities. The use of activated carbon in the first or initial recrystallization stage alone is almost as effective as its use in both stages of a two stage SBPA recrystallization procedure. However, when recrystallization is done with water, it is preferred to preliminarily dry the crude SBPA because any residual acetic acid or other aliphatic carboxylic acid from the oxidation solvent reduces recovery. Presently preferred crude solid SBPA drying conditions involve heating the crude SBPA to a temperature in the range of about 212° F. to about 302° F. (about 100° C. to about 150° C.) and maintaining it at such a temperature for a time period sufficient to reduce the quantity of the oxidation solvent present in the crude SBPA to a level which preferably is below about 5 weight percent of the dried crude SBPA.

Physical separation of a slurried or recrystallized SBPA from the purification solvent can be accomplished by any convenient procedure, including settling, filtration, centrifugation, and the like. Centrifugation or filtration are the preferred separation techniques.

Various slurrying and recrystallization procedures for purifying the crude SBPA were evaluated and are summarized below in Tables VA, VB, and VI which present data obtained in Examples 15-31 that follow.

Sodium salt treatments were also evaluated. Although catalyst metals were almost completely removed, organic impurities were not reduced enough for salt treatments to be considered further.

Two recrystallization procedures using water and a concurrent carbon treatment in the first stage is the presently most preferred purification procedure.

For recrystallization of SBPA from purification solvent, the preferred and most preferred processing conditions are summarized below in the Table III.

TABLE III
PREFERRED RECRYSTALLIZATION PROCESS CONDITIONS

| Variable | Preferred Range | Most Preferred |
|---|---|---|
| Solvent, wt. % acetic acid in water | 0–100 | 0 |
| Solvent ratio[1] | 2–8 | 4.0 |
| Carbon, wt. %[2] | 1.0–5.0 | 3.0 |
| Solution temperature, °F. | 176–302 | 250 |
| Centrifugation temp., °F. | 32–125 | 75 |

TABLE III Footnotes
[1]Weight ratio of purification solvent to SBPA.
[2]Activated carbon, based on weight of SBPA present.

(e) SBPA Dehydration to SPAN

To dehydrate SBPA to SPAN in accord with the process of this invention, SBPA is maintained in the solid state during heating. Thus, the solid SBPA is heated to and maintained at a temperature in the range of about 370° F. to about 500° F. (about 188° C. to about 260° C.) for a time period in the range of about 2 to about 120 hours to effect its conversion to the anhydride. SPAN does not melt until a temperature of about 554° F. (290° C.) is reached.

To avoid possible material agglomeration problems in a dryer, it is preferred to preliminarily dry the SBPA before commencing the dehydration. Presently preferred drying conditions involve holding the SBPA to be dehydrated at a temperature in the range of about 176° F. to about 302° F. (about 80° C. to about 150° C.) for a time period sufficient to reduce the quantity of residual solvent present (oxidation solvent or purification solvent, as the case may be) to a level which is preferably below about 5 weight percent, based on the weight of dried SBPA.

The dehydration time appears to correlate inversely with the purity of the SBPA. In general, the higher purity SBPA materials dehydrate at slower rates than the lower purity SBPA materials.

Also, the weight loss experienced during dehydration is characteristically greater than theoretical, with a crude SBPA losing more weight than a purified SBPA. This circumstance indicates that some impurities are removed by sublimation during the solid state dehydration procedure. Bromine levels are observed to be reduced during dehydration by a factor of about 20; such a reduction in bromine content may be due to the sublimation of bromophthalic anhydride which forms from bromophthalic acid that may be present as an impurity.

If desired, before undertaking a dehydration procedure for a given SBPA, the dehydration rate for that SBPA can be determined for that particular SBPA. For instance, in Example 32 (below), SBPA dehydration rates were measured by an illustrative procedure.

EXAMPLES 1–3

SBPA Preparation and Recovery

Each of Examples 1–3 involved the oxidation of TMPS on a semicontinuous basis. The reactor employed was a two-liter reactor equipped with a stirrer, cooling coil, and a line for introduction of air during the oxidation. The temperature of the reactor was controlled by insulated electric heaters which surrounded the autoclave, as well as by the cooling coil in the reactor. A controlled rate of cooling fluid was passed through the cooling coil during the oxidation. The vented gases from the reactor were passed through a series of condensers, cooled by dry-ice, and then through instruments which recorded the gaseous flow rate and the concentration of oxygen and carbon oxides in the gas stream.

An acetic acid solvent (including water added from an external source—that is, the total of new and recycled solvent—at a concentration of 5 weight percent based on the acetic acid) and the cobalt, manganese (added in the form of their acetate tetrahydrates), and bromine (added as HBr) catalyst components were introduced batchwise into the reactor. The reactor was purged and then pressurized to 300 psig with a slow addition of nitrogen gas. The temperature of the reactor contents was raised to the desired level for commencement of the oxidation. Then a 30-weight percent solution of TMPS in acetic acid (at 240° F.) and at a rate of 6.67 milliliters per minute, and air were introduced continuously into the reactor. The pressure of the reactor was controlled by a research control valve. The rate of oxidation was determined by measuring the oxygen content of the vent gas and the known flow rate of air through the reactor, and was employed as a measure of the extent of reactant conversion. The reaction was terminated after oxygen uptake had ceased and the oxygen content of the vent gas exceeded 10 mole percent. The flow of air into the reactor then was replaced by a flow of nitrogen gas. The final or total weight ratio of acetic acid solvent-to-TMPS (including solvent added with the TMPS) added to the reactor over the duration of the run was 6:1. The reactor effluent was cooled to 75° F. and filtered. The obtained, filtered SBPA cake was dried overnight in a 110° C., 20 in. Hg. vacuum oven. Additional experimental conditions employed in and the results from Examples 1–3 are presented in Table IVA, below.

The procedure of Example 1 was taken as a base or standard case for comparative purposes. Thus, Examples 2 and 3 illustrate the effect of higher and lower operating temperatures as compared to the base of Example 1.

In Tables IVA through IVE, "EGC" designates esterification gas chromatography, and "XRF" designates x-ray fluorescence. Four partial oxidation impurities are two methyltriacid isomers, a diacidphthalide, and a hydroxymethyltriacid. All four impurities appear to track each other with the methyltriacids being the most significant. The two triacid isomers are believed to be decarboxylation products. Phthalic acid, bromophthalic acid, and methyl sulfone are believed to be products resulting from cleavage at the sulfone group.

The recovery of SBPA shown in Tables IVA through IVE (Examples 1–14) was accomplished in all Examples by filtration at 75° F. (23.9° C.).

TABLE IVA 3,3',4,4'-SULFONYL BIS(PHTHALIC ACID) (SBPA) OXIDATION CONDITIONS AND RESULTS

| Variable or Item | Ex. 1 Base | Ex. 2 Low T | Ex. 3 High T |
|---|---|---|---|
| Feed Conditions | | | |
| wt % Co on initial solvent | 0.200 | 0.200 | 0.200 |
| Mn/Co (molar ratio) | 2.0 | 2.0 | 2.0 |
| Zr/Co (molar ratio) | 0.03 | 0.03 | 0.03 |
| Br/metals (molar ratio) | 1.0 | 1.0 | 1.0 |
| wt % $H_2O$ on initial solvent | 5.0 | 5.0 | 5.0 |
| Final Solvent Ratio | 6.0 | 6.0 | 6.0 |
| Process Conditions | | | |
| Feed Rate (g/hr/g solv) | 0.91 | 0.91 | 0.91 |
| TMPS (g) | 124.8 | 124.8 | 124.8 |
| HC Addition Time (min) | 60 | 60 | 60 |
| Tailout (min) | 8 | 10 | 5 |
| Temperature (°F.) | 375 | 350 | 400 |
| Pressure (psig) | 300 | 300 | 300 |
| Vent $O_2$ (mole %) | 5.2 | 6.4 | 5.5 |
| Reduced Results | | | |
| Reactor Yield (mole %) SBPA C + F + W by EGC | 87.1 | 85.6 | 70.9 |
| Product Yield (wt %) (theo. 144 wt %) | 97.8 | 98.5 | 60.8 |
| Vent (mole/mole HC) | | | |
| $CO_x$ Production | 1.48 | 0.91 | 2.87 |
| $O_2$ to Aromatic Acid | 6.70 | 6.69 | 6.26 |
| Accountability | | | |
| Hydrocarbon (mole %) | 95.8 | 93.0 | 84.0 |
| Overall (wt %) | 95.2 | 93.4 | 96.8 |
| Cake Analysis | | | |
| EGC, wt % | | | |
| Phthalic Acid | 0.17 | 0.13 | 0.26 |
| Bromophthalic Acid | 0.20 | 0.65 | 1.66 |
| Methylsulfone | 0.46 | 0.32 | 0.34 |
| Triacid #1 | 0.34 | 0.40 | 0.74 |
| Triacid #2 | 0.50 | 0.40 | 0.45 |
| Methyltriacid #1 | 0.03 | 0.51 | <0.1 |
| Methyltriacid #2 | 0.03 | 0.35 | <0.1 |
| Hydroxymethyltriacid | 0.51 | 0.76 | 0.47 |
| SBPA (difference) | 97.43 | 94.88 | 95.17 |
| Diacidphthalide | 0.05 | 0.48 | <0.1 |
| Unknowns | 0.27 | 1.14 | 0.92 |
| XRF, ppm | | | |
| Co | 570 | 610 | 1060 |
| Mn | 1260 | 1150 | 3120 |
| Zr | 155 | 58 | 93 |
| Br | 640 | 1850 | 2070 |
| O.D. (340 nm)[1] | 1.2 | 1.5 | 2.0 |

Examples 4 and 5: SBPA Preparation and Recovery

The procedure of Example 1 was further repeated twice except that each such repeat procedure was carried out with a different total catalyst content in the catalyst system compared to the catalyst content employed in the base Example 1.

The feed rates, process conditions, and results obtained for each procedure are shown in Table IVB (below). The data from Example 1 are included for comparison purposes. Thus, Examples 4 and 5 illustrate the effect of lower and higher catalyst contents compared to the base catalyst content used in Example 1.

[1] In these and all other runs reported herein the optical density (O.D.) was determined by dissolving SBPA (1 gram) in 4 N $NH_4OH$ (100 ml) and then measuring the absorbance of 340 nm wavelength by the resulting solution in a 10 mm cell. The measured absorbance ($A_{340}$) was then normalized to the standard 50 mm pathlength, i.e., O.D. = 5 ($A_{340}$).

TABLE IVB

3,3',4,4'-SULFONYL BIS(PHTHALIC ACID) (SBPA) OXIDATION CONDITIONS AND RESULTS

| Variable or Item | Ex. 1 Base | Ex. 4 Low Catalyst | Ex. 5 High Catalyst |
|---|---|---|---|
| Feed Conditions | | | |
| wt % Co on initial solvent | 0.200 | 0.100 | 0.400 |
| Mn/Co (molar ratio) | 2.0 | 2.0 | 2.0 |
| Zr/Co (molar ratio) | 0.03 | 0.03 | 0.03 |
| Br/metals (molar ratio) | 1.0 | 1.0 | 1.0 |
| wt % $H_2O$ on initial solvent | 5.0 | 5.0 | 5.0 |
| Final Solvent Ratio | 6.0 | 6.0 | 6.0 |
| Process Conditions | | | |
| Feed Rate (g/hr/g solv) | 0.91 | 0.91 | 0.91 |
| TMPS (g) | 124.8 | 124.8 | 124.8 |
| HC Addition Time (min) | 60 | 60 | 60 |
| Tailout (min) | 8 | 10 | 9 |
| Temperature (°F.) | 375 | 375 | 375 |
| Pressure (psig) | 300 | 300 | 300 |
| Vent $O_2$ (mole %) | 5.2 | 6.1 | 5.7 |
| Reduced Results | | | |
| Reactor Yield (mole %) SBPA C + F + W by EGC | 87.1 | 87.6 | 83.8 |
| Product Yield (wt %) (theo. 144 wt %) | 97.8 | 103.8 | 92.1 |
| Vent (mole/mole HC) | | | |
| $CO_x$ Production | 1.48 | 1.17 | 1.46 |
| $O_2$ to Aromatic Acid Accountability | 6.70 | 6.55 | 6.85 |
| Hydrocarbon (mole %) | 95.8 | 97.0 | 92.2 |
| Overall (wt %) | 95.2 | 95.6 | 93.2 |
| Cake Analysis | | | |
| EGC, wt % | | | |
| Phthalic Acid | 0.17 | 0.17 | 0.16 |
| Bromophthalic Acid | 0.20 | 0.63 | 0.91 |
| Methylsulfone | 0.46 | 0.48 | 0.40 |
| Triacid #1 | 0.34 | 0.47 | 0.40 |
| Triacid #2 | 0.50 | 0.45 | 0.38 |
| Methyltriacid #1 | 0.03 | 0.65 | 0.07 |
| Methyltriacid #2 | 0.03 | 0.48 | 0.05 |
| Hydroxymethyltriacid | 0.51 | 0.68 | 0.55 |
| SBPA (difference) | 97.43 | 95.27 | 96.33 |
| Diacidphthalide | 0.05 | 0.29 | 0.12 |
| Unknowns | 0.27 | 0.44 | 0.64 |
| XRF, ppm | | | |
| Co | 570 | 430 | 1410 |
| Mn | 1260 | 850 | 3560 |
| Zr | 155 | 57 | 108 |
| Br | 640 | 1260 | 2140 |
| O.D. (340 nm) | 1.2 | 1.2 | 2.3 |

TABLE IVC

3,3',4,4'-SULFONYL BIS(PHTHALIC ACID) (SBPA) OXIDATION CONDITIONS AND RESULTS

| Variable or Item | Ex. 1 Base | Ex. 6 No Zr | Ex. 7 Low Zr | Ex. 8 High Zr |
|---|---|---|---|---|
| Feed Conditions | | | | |
| wt % Co on initial solvent | 0.200 | 0.200 | 0.200 | 0.200 |
| Mn/Co (molar ratio) | 2.0 | 2.0 | 2.0 | 2.0 |
| Zr/Co (molar ratio) | 0.03 | 0.00 | 0.01 | 0.06 |
| Br/metals (molar ratio) | 1.0 | 1.0 | 1.0 | 1.0 |
| wt % $H_2O$ on initial solvent | 5.0 | 5.0 | 5.0 | 5.0 |
| Final Solvent Ratio | 6.0 | 6.0 | 6.0 | 6.0 |
| Process Conditions | | | | |
| Feed Rate (g/hr/g solv) | 0.91 | 0.91 | 0.91 | 0.91 |
| TMPS (g) | 124.8 | 124.8 | 124.8 | 124.8 |
| HC Addition Time (min) | 60 | 60 | 60 | 60 |
| Tailout (min) | 8 | 7 | 9 | 7 |
| Temperature (°F.) | 375 | 375 | 375 | 375 |
| Pressure (psig) | 300 | 300 | 300 | 300 |
| Vent $O_2$ (mole %) | 5.2 | 6.8 | 6.2 | 7.0 |
| Reduced Results | | | | |
| Reactor Yield (mole %) SBPA C + F + W by EGC | 87.1 | 73.1 | 81.9 | 68.8 |
| Product Yield (wt %) (theo. 144 wt %) | 97.8 | 68.1 | 92.5 | 71.2 |
| Vent (mole/mole HC) | | | | |
| $CO_x$ Production | 1.48 | 0.88 | 1.31 | 1.21 |
| $O_2$ to Aromatic Acid Accountability | 6.70 | 6.26 | 6.81 | 5.84 |
| Hydrocarbon (mole %) | 95.8 | 88.8 | 89.9 | 75.7 |
| Overall (wt %) | 95.2 | 93.6 | 93.8 | 95.9 |
| Cake Analysis | | | | |
| EGC, wt % | | | | |
| Phthalic Acid | 0.17 | 0.15 | 0.15 | 0.14 |
| Bromophthalic Acid | 0.20 | 0.58 | 0.24 | 1.15 |
| Methylsulfone | 0.46 | 0.58 | 0.34 | 0.34 |
| Triacid #1 | 0.34 | 0.70 | 0.31 | 0.58 |
| Triacid #2 | 0.50 | 0.54 | 0.42 | 0.44 |
| Methyltriacid #1 | 0.03 | 5.6 | 0.28 | 0.10 |
| Methyltriacid #2 | 0.03 | 3.62 | 0.26 | 0.1 |
| Hydroxymethyltriacid | 0.51 | 1.8 | 0.64 | 0.53 |
| SBPA (difference) | 97.43 | 81.63 | 96.97 | 96.54 |
| Diacidphthalide | 0.05 | 1.66 | 0.17 | <0.1 |
| Unknowns | 0.27 | 3.17 | 0.23 | 0.22 |
| XRF, ppm | | | | |
| Co | 570 | 346 | 298 | 990 |
| Mn | 1260 | 1050 | 620 | 2140 |
| Zr | 155 | <2 | 29 | 159 |
| Br | 640 | 1660 | 850 | 2650 |
| O.D. (340 nm) | 1.2 | 3.7 | 1.8 | 0.9 |

EXAMPLES 6, 7, and 8

SBPA Preparation and Recovery

The procedure of Example 1 was repeated three times, except that each such repeat procedure was carried out with a zirconium content different from that employed in the base Example 1. No zirconium was present in Example 6.

The feed rates, process conditions, and results obtained for each procedure are shown in Table IVC (below). The data from Example 1 are included for comparison purposes. Thus, Examples 6, 7 and 8 illustrate the effect of no, lower, and higher zirconium contents as compared to the base zirconium content used in Example 1.

EXAMPLES 9 and 10

SBPA Preparation and Recovery

The procedure of Example 1 was repeated twice except that each such repeat procedure was carried out with a different bromine content from that employed in the base Example 1.

The feed rates, process conditions, and results obtained for each procedure are shown in Table IVD (below). The data from Example 1 are included for comparison purposes. Thus, Examples 9 and 10 illustrate the effect of lower and higher bromine contents compared to the base bromine content of Example 1.

TABLE IVD

3,3',4,4'-SULFONYL BIS(PHTHALIC ACID) (SBPA) OXIDATION CONDITIONS AND RESULTS

| Variable or Item | Ex. 1 Base | Ex. 9 Low Br | Ex. 10 Low Br |
|---|---|---|---|
| Feed Conditions | | | |
| wt % Co on initial solvent | 0.200 | 0.200 | 0.200 |

TABLE IVD-continued 3,3',4,4'-SULFONYL BIS(PHTHALIC ACID) (SBPA)
OXIDATION CONDITIONS AND RESULTS

| Variable or Item | Ex. 1 Base | Ex. 9 Low Br | Ex. 10 Low Br |
|---|---|---|---|
| Mn/Co (molar ratio) | 2.0 | 2.0 | 2.0 |
| Zr/Co (molar ratio) | 0.03 | 0.03 | 0.03 |
| Br/metals (molar ratio) | 1.0 | 0.5 | 0.8 |
| wt % $H_2O$ on initial solvent | 5.0 | 5.0 | 5.0 |
| Final Solvent Ratio | 6.0 | 6.0 | 6.0 |
| Process Conditions | | | |
| Feed Rate (g/hr/g solv) | 0.91 | 0.91 | 0.91 |
| TMPS (g) | 124.8 | 124.8 | 124.8 |
| HC Addition Time (min) | 60 | 60 | 60 |
| Tailout (min) | 8 | 11 | 9 |
| Temperature (°F.) | 375 | 375 | 375 |
| Pressure (psig) | 300 | 300 | 300 |
| Vent $O_2$ (mole %) | 5.2 | 6.3 | 5.7 |
| Reduced Results | | | |
| Reactor Yield (mole %) SBPA C + F + W by EGC | 87.1 | 82.1 | 85.3 |
| Product Yield (wt %) (theo. 144 wt %) | 97.8 | 95.4 | 94.5 |
| Vent (mole/mole HC) | | | |
| $CO_x$ Production | 1.48 | 1.14 | 1.28 |
| $O_2$ to Aromatic Acid | 6.70 | 6.46 | 6.71 |
| Accountability | | | |
| Hydrocarbon (mole %) | 95.8 | 89.6 | 93.3 |
| Overall (wt %) | 95.2 | 94.4 | 94.5 |
| Cake Analysis | | | |
| EGC, wt % | | | |
| Phthalic Acid | 0.17 | 0.16 | 0.13 |
| Bromophthalic Acid | 0.20 | 0.35 | 0.56 |
| Methylsulfone | 0.46 | 0.41 | 0.30 |
| Triacid #1 | 0.34 | 0.37 | 0.43 |
| Triacid #2 | 0.50 | 0.40 | 0.48 |
| Methyltriacid #1 | 0.03 | 0.30 | 0.26 |
| Methyltriacid #2 | 0.03 | 0.27 | 0.21 |
| Hydroxymethyltriacid | 0.51 | 0.75 | 0.67 |
| SBPA (difference) | 97.43 | 96.22 | 96.44 |
| Diacidphthalide | 0.05 | 0.22 | 0.18 |
| Unknowns | 0.27 | 0.54 | 0.34 |
| XRF, ppm | | | |
| Co | 570 | 1160 | 440 |
| Mn | 1260 | 2820 | 950 |
| Zr | 155 | 130 | 79 |
| Br | 640 | 850 | 1260 |
| O.D. (340 nm) | 1.2 | 1.7 | 1.0 |

EXAMPLES 11, 12, 13, and 14

SBPA Preparation and Recovery

The procedure of Example 1 was repeated in each of the present Examples 11, 12, and 13 to illustrate the effects of, respectively, increased feed rate, staged catalyst addition, and staged temperature profile in the oxidation reactor compared to the corresponding conditions employed in the base Example 1.

In Example 11, the feed rate of the 30-weight percent solution of TMPS in acetic acid was increased to 10.67 milliliters per minute. The addition of TMPS feed was terminated after 38 minutes to keep the total charge the same as in Example 1.

In Example 12, only one-half the catalyst a charge used in Example 1 was initially charged into the reactor. Additional catalyst was added over a period of 25 minutes starting 35 minutes after the initiation of the reaction. The final catalyst concentrations were equal to the final catalyst concentrations in Example 1.

In Example 13, the reaction temperature was maintained at 350° F., except for the last 10 minutes of TMPS addition at which time the temperature was allowed to increase to 380° F.

In Example 14, the TMPS was charged into the reactor with the acetic acid solvent and catalyst. The TMPS was then oxidized in a batch mode. The reactor contents were heated to 280° F. and at which time air was introduced continuously into the reactor. The reactor temperature was allowed to increase continuously at a rate of about 2.5° F. per minute over a 40 minute time period, after which time the reaction was terminated.

The feed rates, process conditions, and results obtained for each procedure are shown in Table IVE (below). The data from Example 1 are included for comparison purposes. Thus, the Examples 11-14 illustrate the effect of variations in process conditions upon the base procedure of Example 1.

TABLE IVE 3,3',4,4'-SULFONYL BIS(PHTHALIC ACID) (SBPA)
OXIDATION CONDITIONS AND RESULTS

| Variable or Item | Ex. 1 Base | Ex. 11 Fast Feed | Ex. 12 Staged Cat. | Ex. 13 Staged Temp. | Ex. 14 Batch |
|---|---|---|---|---|---|
| Feed Conditions | | | | | |
| wt % Co on initial solvent | 0.200 | 0.200 | 0.1-0.2 | 0.200 | 0.200 |
| Mn/Co (molar ratio) | 2.0 | 2.0 | 2.0 | 2.0 | 2.0 |
| Zr/Co (molar ratio) | 0.03 | 0.03 | 0.03 | 0.03 | 0.03 |
| Br/metals (molar ratio) | 1.0 | 1.0 | 1.0 | 1.0 | 1.0 |
| wt % $H_2O$ on initial solvent | 5.0 | 5.0 | 5.0 | 5.0 | 5.0 |
| Final Solvent Ratio | 6.0 | 6.0 | 6.0 | 6.0 | 6.0 |
| Process Conditions | | | | | |
| Feed Rate (g/hr/g solv) | 0.91 | 1.46 | 0.91 | 0.91 | batch |
| TMPS (g) | 124.8 | 124.8 | 124.8 | 124.8 | 124.8 |
| HC Addition Time (min) | 60 | 38 | 60 | 60 | 0 |
| Tailout (min) | 8 | 5 | 7 | 9 | — |
| Temperature (°F.) | 375 | 375 | 375 | 350→380 | 280→380 |
| Pressure (psig) | 300 | 300 | 300 | 300 | 300 |
| Vent $O_2$ (mole %) | 5.2 | 5.3 | 5.5 | 6.2 | — |
| Reduced Results | | | | | |
| Reactor Yield (mole %) SBPA C + F + W by EGC | 87.1 | 84.8 | 85.6 | 84.6 | 91.4 |
| Product Yield (wt %) (theo. 144 wt %) | 97.8 | 94.6 | 97.2 | 97.7 | 110.7 |
| Vent (mole/mole HC) | | | | | |

TABLE IVE-continued 3,3',4,4'-SULFONYL BIS(PHTHALIC ACID) (SBPA)
OXIDATION CONDITIONS AND RESULTS

| Variable or Item | Ex. 1 Base | Ex. 11 Fast Feed | Ex. 12 Staged Cat. | Ex. 13 Staged Temp. | Ex. 14 Batch |
|---|---|---|---|---|---|
| $CO_x$ Production | 1.48 | 1.20 | 1.19 | 0.99 | 0.28 |
| $O_2$ to Aromatic Acid Accountability | 6.70 | 6.70 | 6.50 | 6.81 | 6.40 |
| Hydrocarbon (mole %) | 95.8 | 92.1 | 95.4 | 90.8 | 95.0 |
| Overall (wt %) | 95.2 | 93.8 | 97.9 | 93.0 | 96.9 |
| Cake Analysis | | | | | |
| EGC, wt % | | | | | |
| Phthalic Acid | 0.17 | 0.12 | 0.19 | 0.15 | 0.1 |
| Bromophthalic Acid | 0.20 | 0.52 | 1.08 | 0.55 | 0.47 |
| Methylsulfone | 0.46 | 0.29 | 0.45 | 0.36 | 0.20 |
| Triacid #1 | 0.34 | 0.40 | 0.72 | 0.28 | 0.21 |
| Triacid #2 | 0.50 | 0.49 | 0.52 | 0.31 | 0.15 |
| Methyltriacid #1 | 0.03 | 0.03 | 0.60 | 0.06 | <0.1 |
| Methyltriacid #2 | 0.03 | 0.03 | 0.29 | 0.05 | <0.1 |
| Hydroxymethyltriacid | 0.51 | 0.39 | 0.88 | 0.62 | 0.26 |
| SBPA (difference) | 97.43 | 97.18 | 94.97 | 97.09 | 98.62 |
| Diacidphthalide | 0.05 | 0.06 | <0.1 | 0.09 | <0.1 |
| Unknowns | 0.27 | 0.50 | 0.27 | 0.45 | <0.1 |
| XRF, ppm | | | | | |
| Co | 570 | 700 | 500 | 630 | 1270 |
| Mn | 1260 | 1330 | 1020 | 1150 | 2260 |
| Zr | 155 | 93 | 174 | 64 | 119 |
| Br | 640 | 1440 | 2270 | 1470 | 1400 |
| O.D. (340 nm) | 1.2 | 1.1 | 0.7 | 1.6 | 1.0 |

EXAMPLES 15-24

SBPA Purification

In Example 15, crude SBPA was prepared in a manner similar to Example 1 but with the process scaled up by a factor of ten. The procedures were the same as those used in Example 1, except that cooling was effected during the exothermic oxidation by returning cooled, condensed solvent to the reactor and temperature was controlled by increasing and decreasing reactor pressure to decrease and increase the amount of solvent reflux, respectively.

In Example 16, 255 grams of crude SBPA from Example 15 was slurried in a flask with 510 grams of water (2:1 solvent-to-SBPA weight ratio), filtered at 75° F. in a Buchner funnel, and dried at 110° C. in a vacuum oven (20 inches Hg).

In Examples 17, 18, and 19, the reslurried SBPA (about 60 grams) from Example 16 was mixed with respectively, water (Example 17), solvent comprising a mixture of 75 weight percent acetic acid and 25 weight percent water (Example 18), and substantially pure, glacial acetic acid (Example 19). The solvent-to-SBPA weight ratio was 4:1 (about 240 grams of solvent). The SBPA was dissolved in the solvent by heating in a one-liter ZipperClave. The SBPA was recovered from the solution by recrystallization, filtering at 75° F. in a Buchner funnel, and drying at 110° C. in a vacuum oven (20 inches Hg).

In Example 20, 103 grams of crude SBPA from Example 15 was slurried in a flask with 412 grams of water (4:1 water-to-SBPA weight solvent ratio), filtered at 75° F. in a Buchner funnel, and dried at 110° C. in a vacuum oven (20 inches Hg).

In Example 21, 78 grams of the reslurried SBPA from Example 20 was mixed with 312 grams of water (solvent-to-SBPA weight ratio of 4:1), and dissolved by heating in a one-liter ZipperClave. The SBPA was recovered from the solution by recrystallization, filtering at 75° F. in a Buchner funnel, and drying in a vacuum oven at 110° C., 20 inches Hg.

In Example 22, 62 grams of the reslurried and recrystallized SBPA from Example 21 was mixed with 247 grams of water (solvent-to-SBPA weight ratio of 4:1), and dissolved by heating in a one-liter ZipperClave. The SBPA was recovered from the solution by recrystallization, filtering at 75° F. in a Buchner funnel, and drying in a vacuum oven at 110° C., 20 inches Hg.

In Example 23, the 100 grams of crude SBPA from Example 15 was mixed with 398 grams of water (solvent-to-SBPA weight ratio of 4:1) and 3 grams of activated carbon (Nuchar SA-20), and dissolved by heating in a one-liter ZiperClave. The carbon was removed from the solution by filtering at 100° C. through a coarse fritted funnel coated with celite. The SBPA was recovered from the solution by recrystallization, filtering at 75° F. in a Buchner funnel, and drying in a vacuum oven at 110° C., 20 inches Hg.

In Example 24, 64 grams of carbon treated and recrystallized SBPA from Example 23 was mixed with 255 grams of water (solvent-to-SBPA weight ratio of 4:1) and 2 grams of activated carbon (Nuchar SA-20), and dissolved by heating in a one-liter ZipperClave. The carbon was removed from the solution by filtering at 100° C. through a coarse fritted funnel coated with celite. The SBPA was recovered from the solution by recrystallization, filtering at 75° F. in a Buchner funnel, and drying in a vacuum oven at 110° C., 20 inches Hg.

The results from Examples 20 through 24 are compiled in Table VA, below, and indicate that an activated carbon treatment improves the optical density, but does not have a significant effect on other impurities. Also, zirconium was reduced in the activated carbon treatment not by the carbon, but by the subsequent hot filtration step.

TABLE VA

3,3',4,4'-SULFONYL BIS(PHTHALIC ACID) (SBPA) PURIFICATION RESULTS

| Example No. | 15 | 16 | 17 | 18 | 19 | 20 | 21 | 22 | 23 | 24 |
|---|---|---|---|---|---|---|---|---|---|---|
| Solvent | | $H_2O$ | $H_2O$ | 75% HOAc | HOAc | $H_2O$ | $H_2O$ | $H_2O$ | $H_2O$ | $H_2O$ |
| Solvent/SBPA Weight Ratio | | 2:1 | 4:1 | 4:1 | 4:1 | 4:1 | 4:1 | 4:1 | 4:1 | 4:1 |
| Activated carbon | | No | No | No | No | No | No | No | Yes | Yes |
| Cake Analysis | | | | | | | | | | |
| EGC, wt % | | | | | | | | | | |
| Phthalic Acid | 0.17 | 0.20 | 0.13 | 0.15 | 0.15 | 0.18 | 0.13 | 0.13 | 0.12 | 0.13 |
| Bromophthalic Acid | 0.74 | 0.78 | 0.07 | 0.53 | 0.32 | 0.74 | 0.39 | 0.06 | 0.14 | 0.03 |
| Methyl Sulfone | 0.29 | 0.39 | 0.32 | 0.32 | 0.29 | 0.34 | 0.34 | 0.26 | 0.27 | 0.26 |
| Tri Acid #1 | 0.41 | 0.57 | 0.42 | 0.38 | 0.40 | 0.44 | 0.34 | 0.25 | 0.29 | 0.18 |
| Tri Acid #2 | 0.32 | 0.44 | 0.47 | 0.30 | 0.23 | 0.33 | 0.37 | 0.37 | 0.44 | 0.44 |
| Methyl Tri Acid #1 | 0.10 | 0.15 | 0.12 | 0.10 | 0.13 | 0.12 | 0.13 | 0.08 | 0.11 | 0.09 |
| Methyl Tri Acid #2 | 0.05 | 0.07 | 0.07 | 0.04 | 0.04 | 0.04 | 0.06 | 0.06 | 0.08 | 0.08 |
| Tri Acid Alcohol | 0.01 | 0.44 | 0.40 | 0.26 | 0.16 | <0.01 | <0.01 | 0.15 | 0.34 | 0.38 |
| SBPA (difference) | 97.67 | 96.80 | 97.78 | 97.77 | 97.96 | 97.18 | 96.73 | 98.21 | 97.88 | 98.13 |
| Diacidphthalide | 0.19 | 0.16 | 0.22 | 0.16 | 0.18 | 0.08 | 0.21 | 0.16 | 0.22 | 0.20 |
| Unknowns | 0.04 | <0.01 | <0.01 | <0.01 | 0.14 | 0.56 | 1.31 | 0.28 | 0.12 | 0.07 |
| XRF, ppm | | | | | | | | | | |
| Co | 1130 | 650 | 72 | 61 | 680 | 266 | 29 | 3 | 21 | <4 |
| Mn | 2370 | 1210 | 128 | 153 | 1120 | 450 | 48 | 5 | 43 | <4 |
| Zr | 93 | 81 | 19 | 29 | 89 | 80 | 36 | 15 | 7 | 8 |
| Br | 1350 | 1930 | 460 | 1320 | 930 | 1650 | 880 | 284 | 420 | 148 |
| O.D. (340 nm) | 2.5 | 2.0 | 1.2 | 1.0 | 1.2 | 1.9 | 1.2 | 0.8 | 0.7 | 0.5 |
| Recovery (mole %) | | 92.7 | 81.3 | 64.6 | 78.9 | 89.8 | 94.1 | 87.8 | 76.9 | 78.9 |

EXAMPLES 25–28

SBPA Purification

In each of the present Examples 25 through 28, the starting SBPA was prepared as in Example 15.

The crude SBPA materials thus produced were subjected to various dispersion purification procedures using various purification solvents. The results are shown in Table VB (below). Specifically:

In Example 25, no purification was attempted.

In Example 26, crude SBPA from Example 25 (80 grams) was mixed with 321 grams of solvent that was a mixture of 75 weight percent acetic acid and 25 weight percent water (solvent-to-SBPA weight ratio of 4:1), and dissolved by heating in a one-liter ZipperClave. The SBPA was recovered from the solution by recrystallization, filtering at 75° F. in a Buchner funnel, and drying at 110° C. in a vacuum oven (20 inches Hg). The recrystallized SBPA was dehydrated to SPAN by heating in an oven for 32 hours at 200° C. under a nitrogen atmosphere.

In Example 27, crude SBPA from Example 26 (90 grams) and several repeats of Example 26 were mixed with 360 grams of solvent that was a mixture of 75 weight percent acetic acid and 25 weight percent water (solvent-to-SBPA weight ratio of 4:1), and dissolved by heating in a one-liter ZipperClave. The SBPA was recovered from the solution by recrystallization, filtering at 75° F. in a Buchner funnel, and drying at 110° C. in a vacuum oven (20 inches Hg). The twice recrystallized SBPA was dehydrated to SPAN by heating in an oven for 32 hours at 200° C. under a nitrogen atmosphere.

In Example 28, crude SBPA from Example 25 (80 grams) was mixed with 324 grams of water (solvent-to-SBPA weight ratio of 4:1), and dissolved by heating in a one-liter ZipperClave. The SBPA was recovered from the solution by recrystallization, filtering at 75° F. in a Buchner funnel, and drying at 110° C. in a vacuum oven (20 inches Hg). This, once recrystallized, SBPA was recrystallized a second time. 75 grams of recrystallized SBPA was mixed with 300 grams of water (solvent-to-SBPA weight ratio of 4:1), and dissolved by heating in a one-liter ZipperClave. The SBPA was recovered from the solution by recrystallization, filtering at 75° F. in a Buchner funnel, and drying in a vacuum oven at 110° C., 20 inches Hg. The twice recrystallized SBPA was dehydrated to SPAN by heating in an oven for 24 hours at 200° C. under a nitrogen atmosphere.

The analyses of the SBPA produced in Examples 25–28 are given in Table VB, below.

TABLE VB

3,3',4,4'-SULFONYL BIS(PHTHALIC ACID) (SBPA) PURIFICATION RESULTS

| Example No. | 25 | 26 | 27 | 28 |
|---|---|---|---|---|
| Solvent | | 75% HOAc[1)] | 75% HOAc[2)] | $H_2O$ |
| Solvent/SBPA Weight Ratio | | 4:1 | 4:1 | 4:1 |
| Cake Analysis | | | | |
| EGC, wt % | | | | |
| Phthalic Acid | 0.18 | 0.02 | 0.15 | 0.12 |
| Bromophthalic Acid | 0.92 | 0.63 | 0.47 | 0.05 |
| Methyl Sulfone | 0.33 | 0.31 | 0.37 | 0.23 |
| Tri Acid #1 | 0.47 | 0.47 | 0.31 | 0.18 |
| Tri Acid #2 | 0.39 | 0.43 | 0.26 | 0.21 |
| Methyl Tri Acid #1 | 0.04 | 0.04 | 0.06 | 0.02 |
| Methyl Tri Acid #2 | 0.02 | <0.01 | <0.01 | 0.02 |
| Tri Acid Alcohol | 0.12 | 0.20 | 0.19 | <0.01 |
| SBPA | 97.42 | 97.64 | 98.12 | 98.98 |
| Diacidphthalide | 0.10 | 0.11 | 0.08 | 0.09 |

TABLE VB-continued

| 3,3',4,4'-SULFONYL BIS(PHTHALIC ACID) (SBPA) PURIFICATION RESULTS | | | | |
|---|---|---|---|---|
| Example No. | 25 | 26 | 27 | 28 |
| Unknowns | <0.01 | <0.01 | <0.01 | 0.09 |
| XRF, ppm | | | | |
| Co | 1020 | 500 | 329 | 19 |
| Mn | 2140 | 1180 | 830 | 46 |
| Zr | 79 | 81 | 38 | 16 |
| Br | 1630 | 1240 | 880 | 236 |
| O.D. (340 nm) | 2.8 | 1.1 | 0.6 | 0.7 |
| Recovery (mole %) | | 82.8 | 87.7 | 87.9 |

[1] single recrystallization
[2] double recrystallization

EXAMPLES 29-31

SBPA Purification

In each of the present Examples 29, 30, and 31, the starting crude SBPA was prepared by scaling up the conditions used in Example 15, above, for a 100-gallon reactor. The reactor was similar to the one used in Example 15, except for size. The hydrocarbon feed charge was 35 pounds of TMPS. Crude SBPA was recovered from the reactor slurry by cooling to 75° F., centrifuging, and drying.

The purification procedure employed in these Examples involved subjecting each starting crude SBPA to two successive procedures of purification solvent dissolution, recrystallization, and separation. Each recrystallization was performed at least twice to minimize experimental error. The procedure used in Examples 29 and 30 served to evaluate the use of activated carbon treatment as a purification aid in a recrystallization. The procedure used in Example 31 served to evaluate the effect of drying crude SBPA cake prior to a recrystallization procedure.

Crude dried SBPA (175 grams) was mixed with 700 grams of the desired solvent and, optionally, activated carbon (Nuchar SA-20, 3.5 grams) in a flask equipped with heating mantle, reflux condenser and magnetic stirrer. The mixture was heated with stirring and held at a reflux for 30 minutes. In runs using carbon, the mixture was filtered through a bed of filter aid (Celite Hyflo Super-Cel) in a preheated Buchner funnel. This step was omitted in runs without carbon. The solution was then allowed to cool, with stirring, to about 22° C. over a time period of 16 hours. The resulting slurry was filtered through a Buchner funnel, and the obtained filter cake was washed with 87.5 grams solvent of the same composition as the solvent used in the recrystallization. The cake was dried, weighed, and analyzed as shown in Table VI. The filtrate (mother liquor) was dried, and the solids obtained therefrom were weighed.

The yield was determined in two ways. The "cake basis" value in Table VI is the weight of the dried cake divided by the weight of the crude SBPA feed. This value tends to be low because of solids hang-up in the precoat filter. The "mother liquor basis" value in Table VI was determined by difference assuming that any feed SBPA not accounted for in the mother liquor went to product. This value tends to be high because of handling losses. Thus, the true yields are believed to be bracketed by these two reported values.

Based on the results of Examples 25-31, it is concluded that the best first-stage recrystallization yields (about 80%) were obtained with pure water as a solvent. Since crude SBPA as recovered from the oxidation contains acetic acid, it is preferably dried prior to a recrystallization from pure water. When mixtures of water and acetic acid were used, the yields ranged from 51 to 72 percent. The yield losses cannot entirely be due to supersaturation since even a reslurry at room temperature only gave yields of about 81 percent.

Two recrystallizations (or one reslurry followed by one recrystallization) appear to be indicated to produce material with less than about 100 ppm metals. The second recrystallization also reduced the optical density, although the improvement was less than for metals; the reduction in organic contaminants was minor.

In the second recrystallization, yields averaged a respectable 95.3 percent (excluding the run identified in Table VI where aqueous acetic acid was used instead of only water). When reslurried product was recrystallized, however, the second-stage yields averaged only 91.4 percent. A reslurry seems to be less effective in removing some unidentified impurity which causes higher losses in the second stage.

Activated carbon is preferably used in at least one of the two (preferred) stages of recrystallization to reduce optical density, bromine, and metals. For most contaminants, slightly better results were obtained with carbon in the first stage than in the second stage. It is also better from an operational view point to use carbon in the first stage since there is an opportunity to clean up a possible or potential carbon contamination in the second recrystallization. There was no significant improvement when carbon was used in both stages rather than only in one stage.

Using two recrystallizations from water, with activated carbon in the first stage, produce a purified SBPA product yield of about 78 weight percent with bromine and metal impurities being below 100 ppm, provided the crude SBPA cake is first dried before purification is undertaken.

TABLE VI

| SBPA PURIFICATION BY RECRYSTALLIZATION | | | |
|---|---|---|---|
| Feed | | | |
| Example No. | 29 | 30 | 31 |
| Br, ppm | 1950 | 2240 | 1890 |
| Co + Fe + Mn + Zr (XRF) ppm | 8428 | 9280 | 8277 |
| Metals (ICP), ppm[2] | 16800 | 16800 | 17045 |
| Ash, ppm | 39100 | 35500 | 39200 |

TABLE VI-continued

SBPA PURIFICATION BY RECRYSTALLIZATION

| | | | | | | | | | | | | | |
|---|---|---|---|---|---|---|---|---|---|---|---|---|---|
| OD (340 nm) | | 2.68 | | | 2.68 | | | | 2.86 | | | | |
| EGC, % | | 3.64 | | | 3.99 | | | | 3.44 | | | | |
| First Recrystallization | | | | | | | | | | | | | |
| HOAc in Solvent, % | | 50 | 50 | 25 | 25 | 0 | | | 67.5 | 18.8 | | 0 | |
| Solvent Ratio | | 4.0 | 4.0 | 3.0 | 3.0 | 6.0 | | | 5.6 | 4.0 | | 5.7 | |
| HOAc in Wash, % | | 0 | 0 | 0 | 0 | 0 | | | 67.5 | 0 | | 0 | |
| Wash Ratio | | 0.5 | 0.5 | 0.3 | 0.3 | 0.3 | | | 0.5 | 0.5 | | 0.5 | |
| Carbon | | N | Y | N | Y | N | | | Y | Y | | Y | |
| Br, ppm | | 920 | 540 | 910 | 324 | 480 | | | 1380 | 700 | | 500 | |
| Co + Fe + Mn + Zr (XRF) ppm | | 243 | 58 | 1152 | 418 | 218 | | | 44 | 425 | | 115 | |
| Metals (ICP), ppm [2] | | 450 | 133 | 2070 | 706 | 388 | | | 73 | 729 | | 165 | |
| Ash, ppm | | 877 | 264 | 4770 | 1660 | 558 | | | 108 | 1772 | | 394 | |
| OD (340 nm) | | 0.81 | 0.68 | 1.08 | 0.86 | 0.92 | | | 0.74 | 2.82 | | 2.26 | |
| EGC, % | | 2.05 | 2.22 | 2.88 | 1.93 | 1.80 | | | 2.18 | 0.98 | | 0.95 | |
| Yield, %: | | | | | | | | | | | | | |
| Cake Basis | | 59.2 | 51.8 | 67.2 | 45.1 | 79.2 | | | 60.7 | 65.9 | | 75.4 | |
| ML Basis | | 61.0 | 59.5 | 69.2 | 51.0 | 79.3 | | | 68.3 | 72.4 | | 81.1 | |
| Second Recrystallization[1] | | | | | | | | | | | | | |
| Carbon | N | Y | N | Y | N | Y | N | Y | N | Y | Y | Y | N | N |
| Br, ppm | 308 | 323 | 171 | 145 | 329 | 230 | 158 | 127 | 246 | 410 | 248 | 314 | 251 | 99 |
| Co + Fe + Mn + Zr (XRF) ppm | 57 | 20 | 18 | 20 | 153 | 31 | 52 | 37 | 56 | 16 | 14 | 28 | 63 | 16 |
| Metals (ICP), ppm[2] | 102 | 55 | 20 | 36 | 322 | 77 | 91 | 173 | 84 | 73 | 59 | 25 | 79 | 38 |
| Ash, ppm | 165 | 265 | 64 | 163 | 385 | 340 | 204 | 604 | 151 | 251 | 371 | 150 | 282 | 186 |
| OD (340 nm) | 0.52 | 0.39 | 0.34 | 0.28 | 0.69 | 0.55 | 0.56 | 0.40 | 0.80 | 0.72 | 0.39 | 0.34 | 0.74 | 0.76 |
| EGC, % | 1.89 | 1.73 | 1.66 | 1.70 | 1.86 | 1.77 | 1.69 | 1.62 | 2.06 | 2.24 | 2.02 | 1.36 | 2.29 | 3.44 |
| Second-stage Yield, %: | | | | | | | | | | | | | | |
| Cake Basis | 92.4 | 72.0 | 94.9 | 66.5 | 89.2 | 78.1 | 92.9 | 57.9 | 89.8 | 82.9 | 81.2 | 55.7 | 95.2 | 96.3 |
| ML Basis | 95.3 | 94.2 | 95.5 | 95.2 | 94.3 | 93.8 | 95.7 | 92.6 | 94.9 | 97.0 | 94.9 | 74.5 | 95.8 | 96.1 |
| Overall Yield, %: | | | | | | | | | | | | | | |
| Cake Basis | 54.7 | 42.6 | 49.2 | 34.4 | 59.9 | 52.5 | 41.9 | 34.2 | 71.1 | 65.7 | 49.3 | 33.8 | 62.7 | 72.6 |
| ML Basis | 58.1 | 57.5 | 56.8 | 56.6 | 64.9 | 64.9 | 48.8 | 47.2 | 75.3 | 76.9 | 64.8 | 50.9 | 69.4 | 77.9 |

Table VI footnotes:
[1] Run recrystallized and washed with 62.5 percent acetic acid. All other runs used water. The solvent ratio was 5.7; and the wash ratio was 0.5 (based on solids in feed).
[2] Sum of: Al, Ca, Co, Cr, Cu, Fe, K, Mg, Mn, Mo, Na, Ni, Ti, Zn, and Zr.

EXAMPLE 32

Dehydration Rates of SBPA

Figure 4:
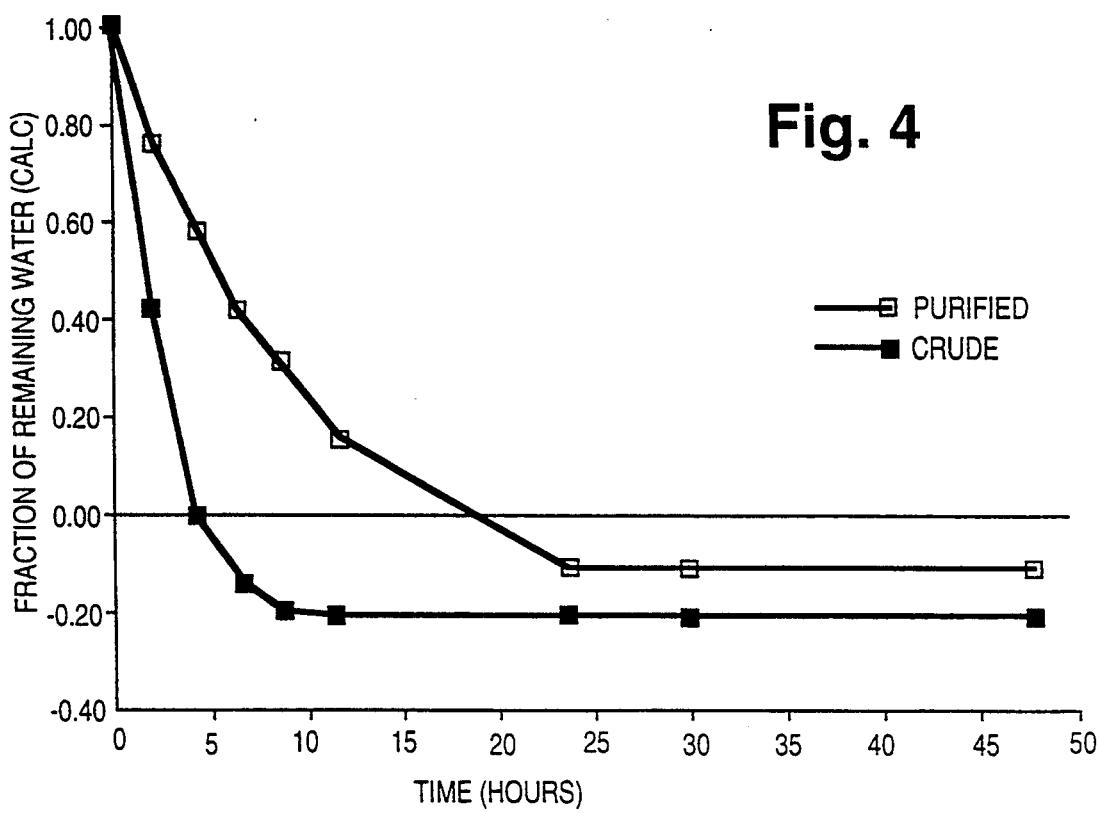
FIG. 4 is a plot of calculated fraction of remaining water versus time and illustrating the rate of solid state dehydration of dried SBPA samples of varying purity at an elevated temperature.

Dehydration rates of SBPA were measured by placing vials of crude SBPA produced as described in Example 15, and purified SBPA produced as described in Example 22 in a 200° C. (392° F.) oven with a 0.05 L/min/g nitrogen purge. Vials were removed at different time increments and their weight losses were recorded. The residual acid was also measured by liquid chromatography to confirm the weight loss measurements. The fraction of remaining water, calculated by weight loss, was plotted as a function of time in FIG. 4.

The results indicated that dehydration is about 99% complete after 2 hours at 200° C. (392° F.) Higher purity SBPA dehydrates at a slower rate than crude SBPA. Also, the crude SBPA lost more weight than the relatively purer SBPA. Such results suggest that some impurities are removed by sublimation. To complete dehydration in a brief time, the SBPA preferably is dehydrated at temperatures higher than 200° C. (392° F.).

Bromine-containing impurities appear to be reduced during dehydration. Dehydration of SBPA is accelerated by a relatively small amount of a heavy metal present in the SBPA.

EXAMPLE 33

Polymer Evaluations

To evaluate the purity of various SPAN products produced by the practice of this invention for use in polymerization, the following procedure was carried out:

Three purified SPAN samples prepared as described above in Examples 26, 27, and 28 were used.

Poly(amic acids) of such SPAN monomers and 4,4'-oxybisanaline (OBA) were made with different ratios of SPAN to OBA. The intrinsic viscosity (IV) of the product polymers was then measured.

A poly(amic acid) product polymer with an (IV) greater than 1.0 dl/g shows that the SPAN monomer is of suitable purity for some polymer applications, The twice recrystallized SPAN produced by Example 27 gave poly(amic acids) with IV's between 0.67 and 1.96 dl/g, depending on the ratio of starting materials. The once recrystallized SPAN produced by Example 26 gave poly(amic acids) with nearly the same IV for two different ratios of SPAN to OPA. In addition, a decrease in ratio from 1.01:1 of SPAN to OBA to 1:1 led to a decrease in IV. Such result suggests the once recrystallized sample may contain significant quantities of both inert diluents and chain stoppers.

The results indicated that SPAN recrystallized once from aqueous 75 percent acetic acid solution has an acceptable purity for some less demanding polymer applications, and that SPAN recrystallized twice from aqueous 75 percent acetic acid solution has an acceptable purity for most polymer applications. Also, SPAN purified by two recrystallizations from purification solvent comprised of 75 weight percent acetic acid and 25 weight percent water, or from water alone gave poly(amic acids) with similar IV's (that is, greater than 1.5 dl/g). Water is the preferred recrystallization solvent because water removes more color and residual catalyst metals.

Although the present invention has been described and illustrated based on the presently available information and embodiments, it is to be understood that modifications and variations are within the spirit and scope of the invention, as those skilled in the art will readily appreciate and that such are within the purview and scope of the appended claims.

We claim:

1. A method for producing sulfonyl bis(phthalic anhydride) comprising the steps of:
   (a) combining, in an oxidation reactor, a liquid admixture of:
      3,3',4,4'-tetramethyl diphenyl sulfone;
      an oxidation solvent comprising an aliphatic carboxylic acid having from 2 to 6 carbon atoms per molecule; and
      an oxidation catalyst soluble in said oxidation solvent and constituted by cobalt, manganese, zirconium, and bromine, at a reactor temperature in the range of about 275° F. to about 440° F. and at a reactor pressure in the range of about 100 to about 400 psig, and maintaining the resulting admixture at said temperature and pressure in the presence of a molecular oxygen-containing gas until a reaction mixture enriched in sulfonyl bis(phthalic acid) is produced;
   (b) recovering sulfonyl bis(phthalic acid) from the resulting reaction mixture by cooling said reaction mixture to crystallize at least some of the sulfonyl bis(phthalic acid) present and separating therefrom solid crystalline sulfonyl bis(phthalic acid); and
   (c) dehydrating said so recovered solid sulfonyl bis(phthalic acid) at an elevated temperature in the range of about 370° F. to about 500° F. by maintaining the recovered sulfonyl bis(phthalic acid) at said elevated temperature for a time sufficient to convert said solid sulfonyl bis(phthalic acid) to sulfonyl bis(phthalic anhydride).

2. The method of claim 1 wherein said oxidation solvent contains no more than about 15 weight percent of water on a total oxidation solvent basis.

3. The method of claim 2 wherein said oxidation solvent initially comprises about 98 to about weight percent of said aliphatic carboxylic acid, and, correspondingly about 2 to about 10 weight percent of water.

4. The method of claim 1 wherein said aliphatic carboxylic acid is acetic acid.

5. The method of claim 1 wherein the weight ratio of said oxidation solvent to said 3,3',4,4'-tetramethyl diphenyl sulfone is in the range of about 2:1 to about 10:1.

6. The method of claim 5 wherein said weight ratio of said oxidation solvent to said 3,3',4,4'-tetramethyl diphenyl sulfone is in the range of about 3:1 to about 8:1.

7. The method of claim 1 wherein the molar ratio of molecular oxygen in said molecular oxygen-containing gas to said 3,3',4,4'-tetramethyl diphenyl sulfone in said reactor is maintained at a value greater than about 6:1.

8. The method of claim 1 wherein said catalyst is constituted by:
   about 4 to about 300 milligram atoms of cobalt calculated as elemental cobalt per gram mole of said 3,3',4,4'-tetramethyl diphenyl sulfone;
   manganese in a mole ratio of manganese to cobalt, calculated as elemental manganese and elemental cobalt, in the range of about 0.5 to about 5; and
   zirconium in a mole ratio of zirconium to cobalt, calculated as elemental zirconium and elemental cobalt, in the range of about 0.01 to about 0.1; and
   bromine in a mole ratio of bromine to the sum of cobalt, manganese, and zirconium, calculated as elemental bromine, elemental cobalt, elemental manganese, and elemental zirconium, in the range of about 0.5 to about 2.

9. The method of claim 1 wherein said cooling is to a temperature in the range of about 50° F. to about 125° F.

10. The method claim 1 wherein said separating of crystallized sulfonyl bis(phthalic acid) is accomplished by filtration or centrifugation.

11. The method of claim i wherein, after said separating, the recovered sulfonyl bis(phthalic acid) is dried prior to dehydration.

12. The method of claim 11 wherein said drying is carried out at a temperature in the range of about 212° to about 302° F. for a time period sufficient to reduce the quantity of oxidation solvent present in the recovered sulfonyl bis(phthalic acid) to a level below about 5 weight percent, based on total weight of dried sulfonyl bis(phthalic acid).

13. The method of claim 1 wherein before said dehydrating the crystalline sulfonyl bis(phthalic acid) is first dispersed in a purification solvent selected from the group consisting of water, aliphatic carboxylic acids having from 2 to 6 carbon atoms per molecule, and mixtures thereof, and then a purified solid sulfonyl bis(phthalic acid) is separated from said purification solvent.

14. The method of claim 13 wherein said purification solvent is selected from the group consisting of water, aliphatic carboxylic acids having from 2 to 6 carbon atoms per molecule, and mixtures thereof.

15. The method of claim 13 wherein said crystalline sulfonyl bis(phthalic acid) is slurried in said purification solvent and then separated therefrom.

16. The method of claim 13 wherein said crystalline sulfonyl bis(phthalic acid) is dissolved in said purification solvent and then recrystallized therefrom.

17. The method of claim 16 wherein said sequence of dissolution, recrystallization, and separation is carried out sequentially at least twice.

18. The method of claim 17 wherein said purification solvent is water.

19. The method of claim 16 wherein the resulting solution of said sulfonyl bis(phthalic acid) is contacted with activated carbon.

20. The method of claim 13 wherein the purified solid sulfonyl bis(phthalic acid) separated from the purification solvent is dried prior to dehydration.

21. The method of claim 20 wherein said drying is carried out at a temperature in the range of about 176° to about 302° F. for a time sufficient to reduce the quantity of said purification solvent in the dried sulfonyl bis(phthalic acid) to a level below about 5 weight percent based on total weight of the dried sulfonyl bis(phthalic acid).

22. The method of claim 13 wherein said purified solid sulfonyl bis(phthalic acid) has a purity level of at least about 95 weight percent prior to dehydration.

23. The method of claim 1 practiced continuously.

24. The method of claim 1 practiced batchwise.

25. The method of claim 1 practiced semicontinuously.

26. A method for producing sulfonyl bis(phthalic acid) by the liquid phase oxidation of 3,3',4,4'-tetramethyl diphenyl sulfone which comprises the steps of:
   introducing into an oxidation reactor 3,3',4,4'-tetramethyl diphenyl sulfone, an oxidation solvent comprising an aliphatic carboxylic acid having 2 to 6 carbon atoms per molecule, an oxygen-containing gas, and an oxidation catalyst system soluble in said oxidation solvent and additionally constituted by cobalt, manganese, zirconium, and bromine;

agitating the resulting reactor contents to produce an admixture;

maintaining the produced admixture in said reactor under liquid phase conditions at a temperature in the range of about 275° F. to about 440° F. and at a pressure in the range of about 100 to about 400 psig for a time period to produce a reaction mixture enriched in sulfonyl bis(phthalic acid);

withdrawing from said reactor an effluent stream having a relatively lower 3,3′,4,4′-tetramethyl diphenyl sulfone content than said admixture and containing sulfonyl bis(phthalic acid);

cooling said effluent stream to a temperature in the range of about 50° F. to 125° F. to crystallize eulfonyl bis(phthalic acid); and separating crystalline sulfonyl bis(phthalic acid) from said effluent stream.

27. The method of claim 26 wherein the weight ratio of said oxidation solvent to said 3,3′,4,4′-tetramethyl diphenyl sulfone is in the range of about 3:1 to about 8:1.

28. The method of claim 26 wherein said oxidation solvent comprises, on a 100 weight percent total oxidation solvent basis, about 98 to about 90 weight percent acetic acid and about 2 to about 10 weight percent water.

29. The method of claim 26 wherein said catalyst is constituted by:

about 4 to about 300 milligram atoms of cobalt calculated as elemental cobalt per gram mole of said 3,3′,4,4′-tetramethyl diphenyl sulfone, manganese in a mole ratio of manganese to cobalt, calculated as elemental manganese and elemental cobalt, in the range of about 0.5 to about 5, zirconium in a mole ratio of zirconium to cobalt, calculated as elemental zirconium and elemental cobalt, in the range of about 0.01 to about 0.1, and bromine in a mole ratio of bromine to the sum of cobalt, manganese, and zirconium, calculated as elemental bromine, cobalt, manganese, and zirconium, in the range of about 0.5 to about 2.

30. The method of claim 26 wherein the molar ratio of molecular oxygen in said molecular oxygen-containing gas to said 3,3′,4,4′-tetramethyl diphenyl sulfone is 6:1.

31. The method of claim 26 wherein said oxygen-containing gas is continuously fed to said reactor at a rate that provides a vent gas oxygen content in the range of about 2 to about 6 volume percent.

32. A method for producing high purity sulfonyl bis(phthalic anhydride) which comprises the steps of:

dispersing a crude sulfonyl bis(phthalic acid) in a purification solvent selected from the group consisting of water, aliphatic carboxylic acids having from 2 to 6 carbon atoms per molecule, and mixtures thereof, separating a purified sulfonyl bis(phthalic acid) in solid form from said purification solvent, heating said so separated solid sulfonyl bis(phthalic acid) at a temperature in the range of about 370° F. to about 500° F. for a time sufficient to dehydrate said sulfonyl bis(phthalic acid) to sulfonyl bis(phthalic anhydride).

33. The method of claim 32 wherein the separated sulfonyl bis(phthalic acid) is preliminarily dried at a temperature in the range of about 176° to about 302° F. for a time sufficient to reduce therein the solvent content thereof to below about 5 weight percent based on weight of dried sulfonyl bis(phthalic acid).

34. The method of claim 32 wherein said crude sulfonyl bis(phthalic acid) is slurried in said purification solvent.

35. The method of claim 32 wherein said crude sulfonyl bis(phthalic acid) is dissolved in said purification solvent and then recrystallized from said solvent.

36. The method of claim 35 wherein, said dissolving is carried out under liquid phase conditions at a temperature in the range of about 176° F. to about 302° F., and recrystallizing is effected at a temperature in the range of about 32° F. to about 125° F.

37. The method of claim 35 in which dissolution and recrystallization are repeated at least once.

38. The method of claim 35 wherein the resulting solution of sulfonyl bis(phthalic acid) is contacted with activated carbon.

39. The method of claim 32 wherein said purified sulfonyl bis(phthalic acid) is dried at a temperature in the range of about 176° F. to about 302° F. for a time sufficient to reduce the quantity of said purification solvent present to a level below about 5 weight percent, based on total weight of said dried sulfonyl bis(phthalic acid), prior to dehydration by heating.

* * * * *

UNITED STATES PATENT AND TRADEMARK OFFICE
CERTIFICATE OF CORRECTION

PATENT NO.: 5,342,968

DATED: August 30, 1994

INVENTOR(S): Stephen P. Brugge; Juergen K. Holzhauer; Thomas E. Wolff

It is certified that error appears in the above-identified patent and that said Letters Patent is hereby corrected as shown below:

| Col. | Line | |
|---|---|---|
| 1 | 44 | "and 4,587,355 to Brown" should read --and U.S. Patent No. 4,587,355 to Brown-- |
| 6 | 49 | "3,3',4,4'1 -tetramethyl" should read --3,3',4,4' -tetramethyl-- |

Signed and Sealed this

Twenty-seventh Day of February, 1996

Attest:

BRUCE LEHMAN

Attesting Officer

Commissioner of Patents and Trademarks